US009921197B2

(12) United States Patent
Yu

(10) Patent No.: US 9,921,197 B2
(45) Date of Patent: Mar. 20, 2018

(54) BOTH ULTRAVIOLET-VISIBLE AND DOUBLE MONOCHROMATIC FLUORESCENCE DUAL DETECTOR FOR HIGH PERFORMANCE LIQUID CHROMATOGRAPHY

(71) Applicant: Jiade Yu, Shanghai (CN)

(72) Inventor: Jiade Yu, Shanghai (CN)

( * ) Notice: Subject to any disclaimer, the term of this patent is extended or adjusted under 35 U.S.C. 154(b) by 100 days.

(21) Appl. No.: 15/042,091

(22) Filed: Feb. 11, 2016

(65) Prior Publication Data

US 2017/0115260 A1     Apr. 27, 2017

(30) Foreign Application Priority Data

Mar. 9, 2015  (CN) .......................... 2015 1 0101048

(51) Int. Cl.
| G01N 30/78 | (2006.01) |
| G01N 21/64 | (2006.01) |
| G01N 30/74 | (2006.01) |
| G01N 21/33 | (2006.01) |
| G01N 30/02 | (2006.01) |

(52) U.S. Cl.
CPC ............ *G01N 30/78* (2013.01); *G01N 21/33* (2013.01); *G01N 21/645* (2013.01); *G01N 30/74* (2013.01); *G01N 2021/6417* (2013.01); *G01N 2030/027* (2013.01); *G01N 2201/068* (2013.01); *G01N 2201/124* (2013.01)

(58) Field of Classification Search
CPC .. G01N 30/64; G01N 2030/626; G01N 30/78; G01N 30/74; G01N 21/645; G01N 21/33; G01N 2201/068; G01N 2030/027; G01N 2021/6417; G01N 2201/124; G01N 2201/1241; G01N 2030/621
See application file for complete search history.

(56) References Cited

U.S. PATENT DOCUMENTS

| 3,972,627 A | * | 8/1976 | Rabl | .................... | G01N 21/272 250/428 |
| 6,115,119 A | * | 9/2000 | Sieracki | ............. | G01N 15/0227 356/337 |

(Continued)

*Primary Examiner* — Que T Le
*Assistant Examiner* — Jennifer Bennett
(74) *Attorney, Agent, or Firm* — Global IP Services; Tianhua Gu

(57) ABSTRACT

A both ultraviolet-visible and double monochromatic fluorescence dual detector has a small inner-casing, which combines both ultraviolet-visible and double monochromatic fluorescence dual detector widely used in the high performance liquid chromatography by taking the first to use deuterium lamp as the individual light source of the dual detectors, the individual sample detection cell and the individual electrical circuit, the device comprises a detection optical member, which including a first monochromatic spectroscopic device—raster G1, a second monochromatic spectroscopic device—raster G2, a light source, four groups of lens needed for processing the light paths; and a detection electromechanical member, which includes: a central controller, a proposed amplifying module, an auto gain module, a noise processing module and a logarithm amplifying module. The dual detector realizes the sensitivity and stability, also the elimination of noise and drift.

8 Claims, 17 Drawing Sheets

(56) References Cited

U.S. PATENT DOCUMENTS

| | | | |
|---|---|---|---|
| 6,666,857 B2 * | 12/2003 | Smith | A61F 9/008 606/11 |
| 7,110,106 B2 * | 9/2006 | Xu | G01N 21/474 356/237.1 |
| 2014/0250984 A1 * | 9/2014 | Yu | G01N 30/64 73/61.58 |

* cited by examiner

BOTH ULTRAVIOLET-VISIBLE AND DOUBLE MONOCHROMATIC FLUORESCENCE DUAL DETECTOR FOR HIGH PERFORMANCE LIQUID CHROMATOGRAPHY

CROSS REFERENCE TO RELATED PATENT APPLICATION

The present application claims the priority of CN 201510101048.6 filed Mar. 9, 2015, which application is incorporated herein by reference.

BACKGROUND OF THE PRESENT INVENTION

Field of the Invention

The present invention relates to the detecting and analyzing instrument, especially to both ultraviolet-visible and double monochromatic fluorescence dual detector for high performance liquid chromatography.

Description of Related Arts

The liquid chromatograph is an instrument for detecting and analyzing organic compound samples quantitatively and qualitatively, and is widely used in petrochemical, medical care, environment protection, food, traditional Chinese/western medicine, beverage, biochemics, and health products etc. to detect and analyze the component of the sample. At present, liquid chromatography mainly comprises high performance liquid chromatography, ion chromatography, capillary chromatography, gel permeation chromatography and the like, wherein high performance liquid chromatography (HPLC) is most widely used.

Liquid chromatography mainly includes a high pressure infusion pump, a high pressure sampling system, a chromatographic column, various detectors and a data processing system connected with the computer. Before the analyzing and detecting process, firstly various mobile phases should be mixed, stirred and degassed, then the sample is prepared into a sample solution which enters into the high pressure sampling system and is delivered into the chromatographic column through the high pressure infusion pump. Since each component of the sample solution has different partition coefficient in two phases, after many times of absorption-desorption partition process, the sample can be separated, as per different time passing the chromatographic column, into chromatographic peak of individual component for the convenience of qualitative analysis, which flowed out in turn from the chromatography column and entered directly into the detector. In the detector, the concentration of each component of the sample is converted to different voltage signals by the detector. After amplifying, zero setting and other processing arts, the output voltage signals are connected with a computer through the data processing system, and the analysis results of the individual component of the sample are saved, displayed and printed in the form of chromatogram and data. From the above content, the stability and detectability of the detector is the key of the whole chromatography instrument. The technical performance of the detector directly decides the technical performance of the whole chromatography instrument, and is an important prerequisite of the accurately qualitative and quantitative analysis of the sample.

In the prior art, ultraviolet visible detector is the earliest as well as the most widely used detector, but it still has heavy technical problems so far: the existing ultraviolet visible detectors cannot overcome or solve the objective existing worldwide technical difficulties: 1. The photoelectric signals generated by the three major components in the optical member of the instrument—lighting lamp, monochromatic device-raster, and receiving photosensitive diode are quite different from each other due to the variation with different wavelengths, and the instrument operates in accordance with Beer-Lambert Law: absorption unit AU=LOG photoelectric signal of incident light/photoelectric signal of transmission light=absorption coefficient×sample concentration (after logarithm), among which the denominator on the right of the equal sign is unknown and the numerator is variable, so none of the existing products can calculate the AU value for each wavelength in the whole wavelength range? As a result, absorption unit AU value of only one optical wavelength can be inspected and calculated, while that of other hundreds of wavelengths cannot be calculated, calibrated, inspected, or checked correctly, but main technical targets in noise and drift indicating the stability of the instrument are calculated and calibrated by absorption unit AU value; as more than 99% of the objective existing wavelengths cannot be calibrated or checked correctly and no technical methods are adopted, technical targets of one wavelength is used to act as different technical targets of other hundreds of wavelengths, and the personnel of inspection agencies are not able to inspect or check so many wavelengths; 2. As there is no special art other than general amplifying processing for weak photoelectric signals, and the simultaneous amplifying of signal together with noise and drift cannot solve the long existing worldwide technical difficulty of the mutual exclusivity and contradiction between sensitivity and stability (i.e. failing to increase the signal to noise ratio), the existing products in the existing production or use have low sensitivity and stability. Therefore, the inspection of samples that should be inspected are often neglected, and it is inevitable that the products are actually not as good as they are described in the publicity documents, and some instruments with wavelength range (190~210 NM) even does not conform to the detection standards and cannot be used, and are actually the "defective products" that cannot be used in the whole wavelengths. More notably, scientific and technical personnel have found that a great number of "DAD diode array ultraviolet detectors" to be used for high performance liquid chromatography, which are produced in some countries and exported to universities and research detection institutions in different countries across the world, actually go against and misuse the theory of "Beer-Lambert Law" studied in physics of middle school: first, monochromatic device without the front of sample detection cell (which is indispensable in practice as well as classical instrument) are introduced in the past trade fairs, and this can be proved by actual products; wavelengths of the front of sample detection cell can only be replaced with those of the back of sample detection cells after spectroscopical process. Actually, this kind of misuse and faking can prove to be the only choice by theories and practice, because the classical and correct set should be the monochromatic component of the front of sample detection cell, and only one photosensitive diode, instead of array of hundreds of photosensitive diodes, is needed to stay close to the back of the detection cell, which shows that components of the array have no practical meaning; secondly, the hybrid light of various wavelengths in front of the sample detection cell enters to the sample detection cell, and actually turns technical targets of optical instruments such as the accuracy, precision, and repeatability of wavelength into dummy false targets and those instruments won't become real optical instruments; thirdly, a lot of non-analytical wavelength's light also have different absorption by the sample and thus generate false photoelectric signals, then such signals will act as analysis wavelength's photoelectric signal and create a hoax of high sensitivity (it can be proved by two absorption peak signals of different wavelengths both sensitive to the same naphthalene sample in Embodiment 1 in Specification); fourth, adding a lot of absorption coefficients of non-analysis wavelengths will lead to relatively large errors in calibration curve compared with that of the classical and standard products, causing the mistake that the result of quantitative analysis is different from that of the classical products; fifth, more chromatographic peaks of other wavelengths to unknown impurities in sample will be generated, and it will be mistaken for high detectting ability.

Fluorescence spectroscopical detector can be classified into: spectroscopical component with low-grade of one monochromator and high-grade of two monochromators. As the high-grade double monochromator spectroscopical component is far difficult than the single monochromator component of ultraviolet detector, the photocurrent signal generated by the secondary emission wavelength will be extremely weak (lower than that of the ultraviolet by 4~5 orders of magnitude). Therefore, smaller signal-to-noise ratio and extremely bad stability will be generated, causing great difficulty in development, and it is hard to meet necessary standards in technical performance. This explains that no products used in the liquid chromatographic high-grade fluorescence have been successfully developed in China, and fluorescence detectors with high performance in liquid chromatograph containing double monochromator are also rarely seen in other countries. Most of them are low-grade fluorescence detector with only one monochromator. In addition, for such detector has no special art in the elimination of noise and drift to increase signal-to-noise ratio, there is no doubt that the technical performance is worse than that of ultraviolet. The excitation wavelength or the emission wavelength cannot be correctly decided even if sample of high concentration are needed for the detection of chromatographic peaks to appear. These two wavelengths should be known, but in fact now one of them is unknown, which brings great difficulties to researchers conducting qualitative analysis of many unknown samples.

SUMMARY OF THE PRESENT INVENTION

In light of the said technical problems existing in the prior art, the present invention adopts three major ideas and methods: 1. problems of incomplete technical targets in the whole wavelength range of ultraviolet detector can only be solved by using auto gain art, 2. Excellent technical performance of both ultraviolet and fluorescence detectors can be largely increased and the objectively existing worldwide technical difficulty of the conflict between sensitivity and stability can perfectly be overcome only by adopting the dual-purpose technology that can be used for both auto elimination of noise of the instrument and reduction of drift; 3. Only by replacing xenon lamp which is short of stability and large drift in thermal diffusion with deuterium lamp that is more stable and lower energy can increase the signal-to-noise ratio of the instrument, which is conducive to realizing better technical performance of fluorescence whose development is quite difficult. The present invention aims at providing the detection and analysis with a novel design, an innovative structure and art, excellent sensitivity and stability, which guarantees that the present art takes the first to use deuterium lamp as the light path of individual light source of fluorescence detector, and a sample detection cell and single electric circuit provided both ultraviolet-visible and double monochromatic fluorescence dual detector for HPLC.

In order to achieve the abovementioned object, the present invention provides both ultraviolet-visible and double monochromatic fluorescence dual detector for HPLC, including a casing with a power supply socket, the casing is provided with a sample solution inlet and a sample solution outlet, a control panel having an operation keyboard and a liquid crystal display, and a detection signal output interface, in the said casing is further provided a detection optical member and a detection electromechanical member, wherein the detection optical member and the detection electromechanical member includes:

Detection optical member: including raster G1 of the first monochromatic spectroscopic device used for both ultraviolet visible wavelength and fluorescence excitation wavelength, raster G2 of the second monochromatic spectroscopic device used for fluorescence emission wavelength, and the light source, four groups of lens needed for processing the light paths, two groups of photosensitive diode for receiving ultraviolet and fluorescence photoelectric signals respectively, and a sample detection cell shared by ultraviolet and fluorescence detection which is connected with the said sample solution inlet and outlet.

Detection electromechanical member: connected with the said operation keyboard and the liquid crystal display of the control panel;

The positive terminals of the said two photosensitive diodes of the ultraviolet and fluorescence monochromators which are used to receive photoelectric signals are respectively controlled by the central controller through the shift switch K1 of the first relay and are earthed, and the negative terminals are connected in parallel and also connected with the inverting input terminal of the first operational amplifier of the preposed amplifying module;

Preposed amplifying module: including the first operational amplifier, and the two input terminals of this first operational amplifier are connected with the parallel connection junctions of the negative terminal of the photosensitive diode and the earth respectively, and the first output terminal is connected with the fixed head of another shift switch K2 of the first relay, and the changeable head is synchronized with the shift switch K1 of the input terminal, and the two resistances maintaining feedback are corresponding to the ultraviolet and fluorescence working state respectively, the input photocurrent signals are converted into voltage signals in the preposed amplifying module and then are amplified;

Auto gain module: at first, photomultiplier has been successfully used as the receiving components of photoelectric signals to impose input photocurrent of the preposed amplifier on the increase or reduction of negative high voltage of the photomultiplier through the control of the central controller composed of microcomputers, to realize the auto control of the designed constant value of the voltage of the first output terminal of the preposed amplifier in the whole wavelength range, with the purpose of realizing the auto gain in analog mode; the present invention gives full play to the microcomputer digital operation's advantages of quickness, accurateness, and non-interference in a digital way: including that the auto gain module 1 and the auto gain module 2 are composed respectively of analog/digital-digital/analog convertor 1 and digital/analog convertor 2, with the input terminal of analog/digital-digital/analog convertor 1 connected with the first output terminal of the preposed amplifier and the output terminal connected with the input terminal of the second operational amplifier, and the central controller composed of microcomputer converts the voltage signals of the preposed amplifier into digital signals, then amplifies and subtracts the digital signals, and when used for ultraviolet detection, the voltage values after the digital signals of various wavelengths in the whole wavelength range are converted into analog signals in digital/analog convertor 1 can be kept the same, and thus the auto gain purpose can be achieved, while used for fluorescence detection, converting the amplified digital into analog voltage values can be realized by amplifying some sample detection signals with relatively good signal-to-noise ratio; for both the detectors, the central controller deposits the digital signals of the analog/digital-digital/analog convertor 1 in the digital/analog convertor 2, and different digital signals in dynamic and static state are converted into voltage difference value which is output to the input terminal of the second operational amplifier, to make the noise processing module conduct processing to noise;

Noise processing module: including a second operational amplifier, whose positive input terminal is connected with the output terminal of analog/digital-digital/analog convertor 1, and the negative input terminal is connected with the output terminal of digital/analog convertor 2, to be used for the elimination of noise and drift of the instrument;

Logarithm amplifying module: including a third operational amplifier and a fourth operational amplifier. The input terminal of the third operational amplifier is connected with the second output terminal of the second operational amplifier, and the input terminal of the fourth operational amplifier is connected with the fixed head of the shift switch K3 of the second relay. The central controller switches the second relay correspondingly during the ultraviolet and fluorescence detection, and the output terminal of the fourth operational amplifier outputs the amplified sample voltage signals through detection signal output interface.

Further, the said preposed amplifying module also includes a first resistance, a second resistance, with one terminal of each resistance connected with the first inverting input terminal of the first operational amplifier, and the other terminal connected with the first output terminal of the first operational amplifier through the shift switch K2 of the first relay, and the said first relay is driven by the said central controller.

Further, the said noise processing module also includes a third resistance, a fourth resistance, a fifth resistance, and a first capacitor, with the said in-phase input terminal of the second operational amplifier connected with the output terminal of the analog/digital-digital/analog convertor 1 through the third resistance, the inverting input terminal of the second operational amplifier connected with the output terminal of digital/analog convertor 2 through the fourth resistance, the output terminal of the second operational amplifier connected with the input terminal of the logarithm amplifying module, one terminal of the said fifth resistance connected with the second inverting input terminal and the other one connected with the second output terminal, and the said first capacitor connected in parallel with the fifth resistance.

Further, the said logarithm amplifying module also includes a sixth resistance, a seventh resistance, a eighth resistance, a ninth resistance, a tenth resistance, and a double transistor Tr1 and Tr2; the said inverting input terminal of the third operational amplifier is connected with the output terminal of the second operational amplifier through the sixth resistance, and the in-phase input terminal of the third operational amplifier is earthed, and the output terminal of the third operational amplifier is connected with two emission electrodes of double transistor through the seventh resistance, and the collector electrode and base electrode of transistor Tr1 are respectively connected with the inverting input terminal of the third operational amplifier and earth, and the collector electrode and base electrode of transistor Tr2 are respectively connected with the first changeable head of shift switch K3 of the second relay and the eighth resistance, and the other terminal of the eighth resistance is connected with direct voltage +V, and the in-phase input terminal of the fourth operational amplifier is connected with the fixed head of shift switch K3 of the second relay, and the other changeable head is connected with the output terminal of the second operational amplifier, and the inverting input terminal of the fourth operational amplifier is connected with one terminal of both the ninth resistance and the tenth resistance, and the other terminal of the ninth resistance is connected with the output terminal of the fourth operational amplifier, and the other terminal of the tenth resistance is earthed, and the output terminal of the fourth operational amplifier is connected to the detection signal output interface.

With the above arrangement and technical processing, both ultraviolet-visible and double monochromatic fluorescence dual detector for HPLC of the present invention has the following distinct characteristics:

In this invention, three unique technologies have been adopted: first, optical structure design uses individual light source and light route and individual sample detection cell to replace the two different light sources and two different sample detection cells for two detectors; in particular, besides the use of high-power xenon lamps, the present art takes the first to use stable low energy-consumption deuterium lamps as the light source of the fluorescence detector and can thus realizes the double monochromatic spectroscopical detection function of high-grade fluorescence detector. In addition, an individual electrical circuit is used to replace two different sets of electrical circuits in two detectors; second, during the ultraviolet detection, the auto gain art is adopted to perfectly overcome the problem of the incomplete technical targets and the difficulty to calculate, calibrate, inspect and test hundreds of wavelengths but not only one wavelength, which have been existing in other ultraviolet detectors in use and production, while the present invention can maintain the main technical targets in the whole wavelength range (190~700 NM): the technical targets of noise and drift (namely the stability) is integral to the calculation, calibration, inspection, and test in an easy and convenient way; on the other hand, the dual-purpose technology is adopted for both auto elimination of the instrument's noise and reduction on the drift, so that the sensitivity, stability, and cost performance of the two detectors can be largely increased, to eventually make sure sample components can be detected and analyzed sensitively and accurately; the present art takes the first in a small inner-casing to realize the detection of both ultraviolet-visible and double monochromatic fluorescence dual detector for HPLC, and therefore the application range of the detector is effectually expanded.

DETAILED DESCRIPTION OF THE PREFERRED EMBODIMENTS

Figure 1:
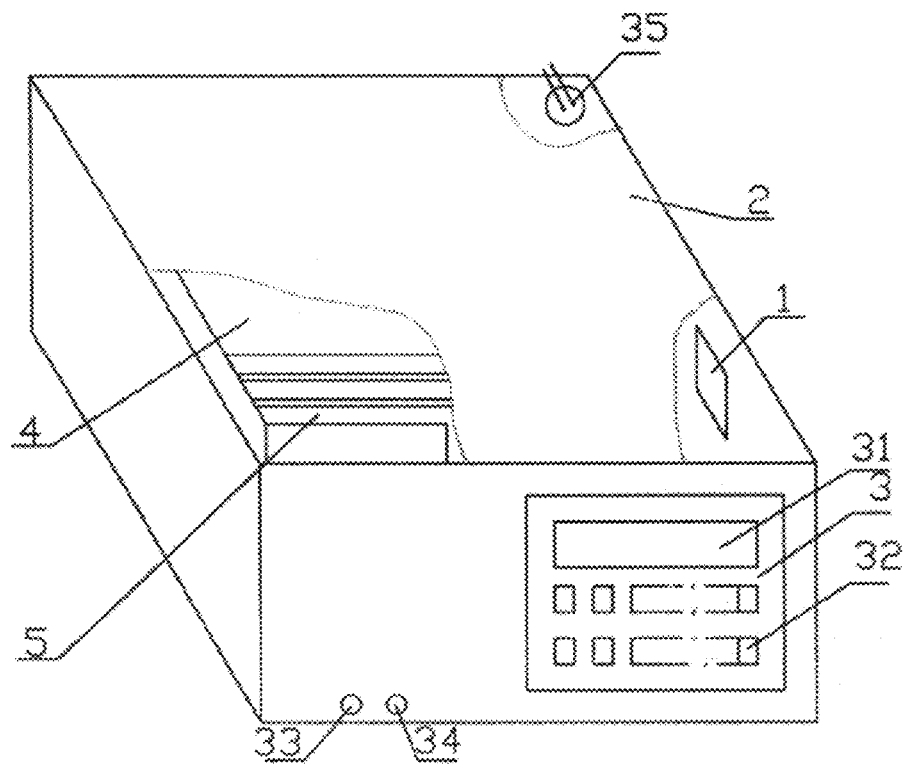
FIG. 1 is a structural diagram of the present invention.
Figure 2:
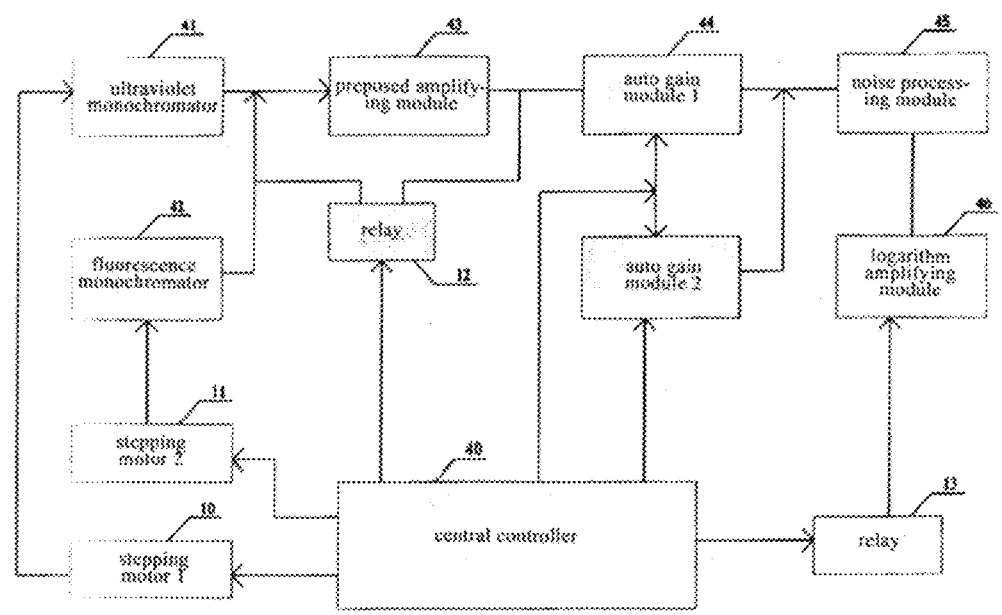
FIG. 2 is an electrical schematic diagram of a detection electromechanical member of the present invention.

In the following text, the invention will be explained in an exemplary fashion on the basis of specific embodiments.

It should be understood that the form, the scale, the size and the like shown in the drawings attached in this specification are all simply used to match with the content exposed by the specification for the skiller in the art understanding and reading, but not used to limit qualifications when the invention may be implemented. Meanwhile, terms such as "up", "down", "left", "right" and the like cited in this specification are also simply for clearness of the description but not used to limit the scope implemented by the invention. The change or the adjustment of the relative relation should also be seen as the scope of the invention when there is no substantial alternation in the technical content.

As shown in FIG. 1, the present invention provides both ultraviolet-visible and double monochromatic fluorescence dual detector for HPLC which includes a casing 2 provided with a power supply socket 1. The said casing 2 is provided with a sample solution inlet 33, a sample solution outlet 34, a control panel 3 provided with a liquid crystal display 31 and an operation keyboard 32, a detection signal output interface 35. The said liquid crystal display 31 is used for tracing and displaying the working state of the detector, and facilitates to know whether the detector works normally through observation, further to determine whether the operation of the operation keyboard 32 or adjustment is needed. When the detector is inserted in the liquid chromatography, the said sample solution inlet 33 is in connection with the outlet of the chromatographic column of the chromatography, the said detection signal output interface 35 is connected with a chromatographic data processing system and a computer. The casing 2 is further provided with a detection optical member 4 and detection electromechanical member 5: they are used for detecting sample components, and the detection optical member is used to provide the detection to samples in sample detection cell with the analysis wavelength selected by the user by passing hybrid light of various wavelengths emitted by the light source through monochromatic spectroscopic device; the detection electromechanical member is used for the technology processing such as amplifying, auto gain, eliminating noise and drift etc. to the photoelectric signals of various detected sample components.

Figure 3:
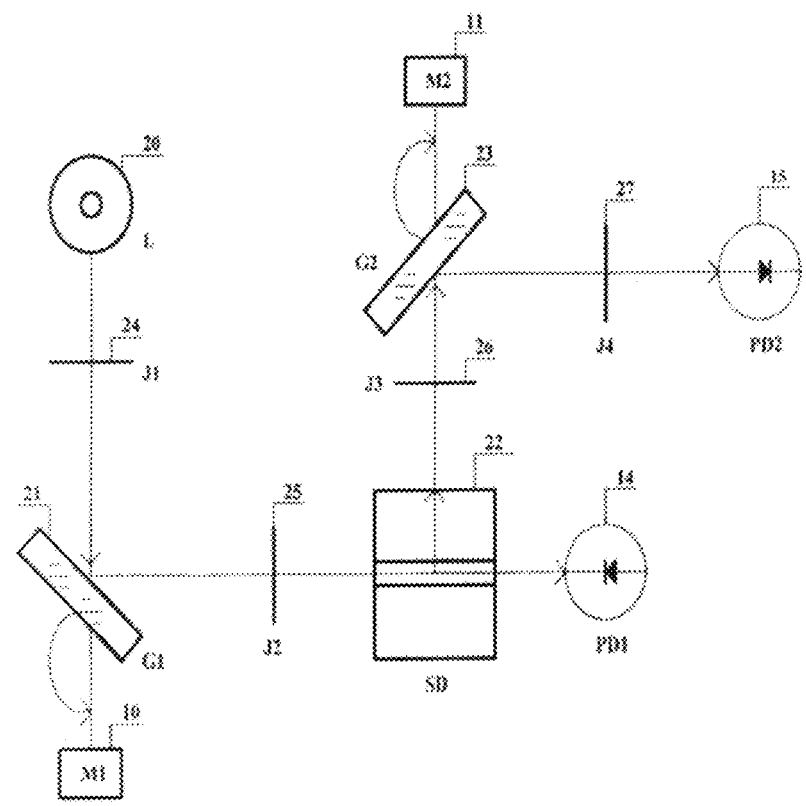
FIG. 3 is an optical schematic diagram of a detection optical member of the present invention.

The said detection optical member 4, as shown in FIG. 3, includes:

Ultraviolet monochromator 41: including light source 20, optical lens 24, a first monochromatic spectroscopic device 21, optical lens 25, sample detection cell 22 and a first photosensitive diode 14;

Fluorescence monochromator 42: including the monochromator part of the first fluorescence excitation wavelength: all components of ultraviolet monochromator 41 except the said first photosensitive diode 14, namely, ultraviolet wavelength also used as fluorescence excitation wavelength; including the monochromator part of the fluorescence secondary emission wavelength: optical lens 26, a second monochromatic spectroscopic device 23, optical lens 27 and a second photosensitive diode 15;

Light source 20: emits hybrid light from ultraviolet to visible continuous wavelengths. The present invention adopts two light sources: first, the relatively high-power xenon lamp of 160 watts; preferably, the present art takes the first to use stable and low energy-consumption deuterium lamp of 25 watts.

The first monochromatic spectroscopic device 21: used as the raster G1 of monochromatic spectroscopic device for both ultraviolet visible and fluorescence excitation wavelengths. The said central controller 40 drives the stepping motor 10 according to the sine rule of optical equation to execute analysis wavelength selected by operation keyboard 32, and then various analysis wavelengths needed after monochromatic spectroscopic processing are generated, and light reflected by them enter into the sample detection cell;

Sample detection cell 22: sample detection cell 22 intercommunicates with the said sample solution inlet 33 and the sample solution outlet 34, and during ultraviolet detection, the analysis wavelengths selected by the first monochromatic spectroscopic device 21 directly irradiate through the sample detection cell to the photosensitive diode 14 in a very short distance behind the detection cell; then, during fluorescence detection, analysis wavelengths selected by the first monochromatic spectroscopic device 21 are used as fluorescence excitation wavelengths, which excite sample solution, to produce new wavelengths radiating in all directions that are different from incident excitation wavelengths, namely secondary emission wavelengths. Unknown emission wavelengths excited will radiate in all directions but will pass through the sample detection cell in a designed direction, and be detected and analyzed as well as determined the correct emission wavelength value by the fluorescence monochromator 42. Pressing button U or F on operation keyboard 32 on the panel can respectively gets the ultraviolet or fluorescence detectors started to work;

Preferably, the said sample detection cell both for direct irradiation and radiation has high light transmittance and is composed of quartz cell that possesses good leakproofness for mobile phase and sample solution with the function of auto continuous analysis, a high sample distinguishability and extremely small sample detection cell volume of 10 micro liters, suitable for both ultraviolet-visible and double monochromatic fluorescence dual detector for HPLC; it's worth pointing out that ultraviolet and fluorescence spectrophotometers used in common laboratories are several hundred times (2~3 milliliters) larger in the sample cell volume, without leakproofness, and many kinds of samples have to be manually changed, and are also difficulty in separating mixed samples and determining their nature;

The second monochromatic spectroscopic device 23: used as the raster G2 of monochromatic spectroscopic device of fluorescence emission wavelength. The said central controller 40 drives raster G2 to rotate by driving stepping motor 11 according to sine rule of optical equation. The emission wavelengths generated by the sample components in the sample detection cell can be determined, and the emission lights reflected by them directly irradiate to the second photosensitive diode 15. The Photoelectric signals are thus generated for the convenience of detecting and analyzing;

Optical lens 24: to meet the technical requirements of the first monochromatic spectroscopic device: the raster 21, the hybrid wavelength light generated by the said light source 20, is converted into parallel light before it is incident on the first monochromatic spectroscopic device: raster 21;

Optical lens 25: focus the monochromatic light reflected after the spectroscopic processing of the said first monochromatic spectroscopic device 21 on the sample detection cell;

Optical lens 26: the light of emission wavelength generated after the excitation of the said sample detection cell is converted into parallel light before it is incident on the second monochromatic spectroscopic device: raster 23;

Optical lens 27: focus the light of emission wavelength reflected after the spectroscopic processing of the said second monochromatic spectroscopic device 23 on the second photosensitive diode 15 for fluorescence detection and analysis;

The first photosensitive diode 14: the said first photosensitive diode is close to the back of the sample detection cell, receiving the ultraviolet light transmitted by the sample detection cell 22, and the photoelectric signals generated are input to the inverting input terminal of the first operational amplifier 6;

The second photosensitive diode 15: the fluorescence light are radiated after the excitation of the sample components input by the said sample detection cell 22, and through optical lens 26, the secondary fluorescence emission wavelengths are determined by the second monochromatic spectroscopic device 23. The emission light reflected by them are focused to the second photosensitive diode 15 through optical lens 27, and the photocurrent signals generated are input into the inverting input terminal of the first operational amplifier 6. The ultraviolet or fluorescence detection and analysis is executed by central controller 40 according to the selection of panel operation key U or F.

The said detection electromechanical member 5 includes:

Central controller 40: composed of microcomputer (including central controller, analog/digital-digital/analog convertor 1 and digital/analog convertor 2, program actuator), and connected with the operation keyboard 32 and liquid crystal display 31 of the said control panel 3;

Preposed amplifying module 43: including a first operational amplifier 6, whose inverting input terminals 61 connected with the first photosensitive diode 14 of the ultraviolet monochromator 41 and the second photosensitive diode 15 of the fluorescence monochromator 42 respectively, and its in-phase input terminal 62 earthed; the said central controller 40 used to control the work state of the two synchronized shift switches K1 and K2 of the first relay: during ultraviolet detection, the shift switch K1 is connected with the said first photosensitive diode 14, and the shift switch K2 connected with the resistance R1; during fluorescence detection, the shift switch K1 is connected with the said second photosensitive diode 15, and the shift switch K2 connected with the resistance R2, and the input photocurrent signals are output through the first output terminal after being converted into the amplified voltage signals of ultraviolet or fluorescence detection;

Auto gain module 44: including analog/digital-digital/analog convertor 1 and digital/analog convertor 2. As the microcomputer conducts the operation in a digital way, the voltage signals of the first output terminal of the first operational amplifier 6 are converted into digital signals by the central controller in the analog/digital-digital/analog convertor 1, and then digital signals are amplified or subtracted. The function of auto gain is to make sure the output voltage of the analog/digital-digital/analog convertor 1 can reach the designed constant voltage value in various analysis wavelengths during ultraviolet detection; during fluorescence detection, if a condition of relatively better signal-to-noise ratio can be achieved, the digital signals obtained from the experiment just need to be amplified, and for both the detectors, the central controller deposits the digital signals of the analog/digital-digital/analog convertor 1 in the digital/analog convertor 2, and the analog voltage difference values of different change and conversion in static and dynamic state are output to the inverting input terminal of the second operational amplifier of the noise processing module, to conduct the noise processing of the second operational amplifier;

Noise processing module 45: including the second operational amplifier 7, whose positive phase input terminal connected with the output terminal of the analog/digital-digital/analog convertor 1, and the inverting input terminal connected with the output terminal of digital/analog convertor 2. Such setup can be used for depositing and tracing the static and dynamic state as well as noise and drift of the instrument generated in pre-stage circuit module that will generate the different-value voltage that will change in various ways, to realize the input of different-value voltage into the second operational amplifier 7 in an inverting input way, so as to eliminate dynamic noise and drift of the instrument, and maintain the long-term stability;

Logarithm amplifying module 46: including operational amplifier 8 and 9, as well as double transistor Tr1 and Tr2, resistance R6, R7, R8, R9, and R10. During ultraviolet detection, the logarithm processing directly to the analog voltage of the second output terminal of the noise processor 45 is easier and more convenient than the logarithm operation of the digital signals converted by another central controller composed of microcomputer, and it will maintain a good accuracy and wide linear range after logarithm processing. Double transistor Tr1 and Tr2 and operational amplifier 8 can be used to realize logarithm processing, and then the amplifying process can be conducted through operational amplifier 9, with the fourth output terminal connected with the detection signal output interface 35. As during the fluorescence detection, it is unnecessary to make logarithm, and all that needed is amplifying directly. Therefore, the said central controller 40 controls the second relay 13, and the shift switch K3 switches to make the stable voltage signal of the second output terminal of the noise processor directly input into the in-phase input terminal of the operational amplifier 9, and then output it through the fourth output terminal after it is amplified by the operational amplifier 9. The sample detection signals through the detection signal output interface 35 are transmitted to chromatographic data processing system, and eventually, detection and analysis results of the sample signals and the sample solution's various components are displayed, saved and printed by the computer in the form of chromatogram and data.

This dual detector of both ultraviolet visible and double monochromatic fluorescence can sensitively, stably, and accurately detect ultraviolet, and especially the sample detection signal of fluorescence emission wavelengths which is weaker than ultraviolet by 4~5 orders of magnitude; it shows that only the high amplification can improve the detecting-ability, but if the detection signals and noise, drift are amplified simultaneously, the noise and drift in signal-to-noise ratio have to be reduced largely to meet the said excellent technical performance; in the detection optical member, the monochromator of fluorescence excitation wavelength is integrated with the monochromator, light source, and sample detection cell of the ultraviolet detection to reduce the volume, structure and cost largely in optical member, so as to create conditions for successfully developing two most commonly used high-quality detectors in one inner-casing; in addition, two distinct innovative technologies are used in the detection electromechanical member: first, auto gain technology is used to overcome and solve HPLC's problems which objectively exist in ultraviolet visible detectors in use or in production, including its low sensitivity and incomplete technical targets problem that only one optical wavelength can while other hundreds of wavelengths cannot be calculated, calibrated, inspected and tested to their main technical targets (noise and drift of the instrument); second, the dual-purpose technology that noise of the instrument can be eliminated automatically and at the same time drift of the instrument can also be reduced is used to overcome the difficulty in improving the signal-to-noise ratio that has existed in all photoelectric instruments for a long time, and to perfectly solve the worldwide technical problem of the exclusion and contradiction between sensitivity and stability, so that the excellent technical performance of the instrument can be achieved.

In this application, the control panel 3 is further provided with the liquid crystal display 31, which facilitates an automatic monitoring of selected values of selected wavelengths, working voltage, and sensitivity as well as various normal working states of the instrument. The operation keyboard 32 includes a plurality of operation keys: the optical operation keys include: numeric keys 0, 1, . . . 9 of wavelength selection, wavelength confirmation key, return key (returning to the commonly used wavelengths that have been set after power on), ultraviolet set key U, fluorescence set key F, and light source key (turn on the light source); the electrical operation keys include: sensitivity selection key, automatically zero set key, auto gain key, and noise processing key, with an alphabetic character or number marked on each of the plurality of keys. After the detector inserted in the chromatography, firstly the power supplies of the high pressure infusion pump and the detector are turned on, then the high pressure infusion pump begins to deliver solution to the single or mixed well-degassed mobile phase. As the mobile phases in the whole instrument from the chromatographic column to the detector is in a normal state of fluid flow, press three-bit number of number keys on operation keyboard 32 in turn to determine the selected analysis wavelengths after selecting operation keys of panel U ultraviolet or F fluorescence, then liquid crystal display 31 will display the wavelength values selected by ultraviolet or fluorescence. During the fluorescence detection, the selected wavelength of the ultraviolet operation key U is the fluorescence excitation wavelength, and the selected wavelength of fluorescence operation key F is the secondary emission wavelength of the fluorescence generated. Next, press the wavelength confirmation key of the operation keyboard 32, and the said central controller 40 drives stepping motor 10 to drive the first monochromatic spectroscopic device 21 and drives stepping motor 11 to drive the second monochromatic spectroscopic device 23 respectively so as to reach the place of the correct wavelength. It often takes about an hour from the solution supply to the preheating and stabilizing of the detector, which is the dynamic preheating and to-be-stabilized state of the detector before sample detection and analysis; After the instrument is stable, in order to sensitively, repeatedly and accurately detect the sample, the detector is firstly properly adjusted as follows before the sample solution is entered: the control sensitivity selection key is controlled by the central controller 40 to select the sensitivity needed, and the auto gain key and the automatically zero set key are adjusted once just before the sample solution is initially entered. In the case of constant analysis condition and stable instrument, it is unnecessary to adjust the two keys frequently; if dynamic drift and variable noise of the instrument are over a certain range allowed, the noise processing key should be pressed so that central controller 40 can calibrate, trace, re-deposit, and eliminate noise and drift timely. Therefore, the noise processing key is determined whether needed to be adjusted according to the condition of voltage variation and chromatographic baseline shown in the liquid crystal display 31 or the computer's chromatogram before the sample is entered every time. And there is no need to adjust the noise processing key if the instrument is in a steady and normal state; the central controller 40 is used in the noise processing module to automatically trace, deposit, and calculate digital signals to eliminate dynamic noise and drift of the instrument. After the afore-said adjustment, the sample solution is then entered into the high pressure sampling system of the chromatography. The sample solution is delivered into the chromatographic column by the high pressure mobile phase of the high pressure infusion pump, and then is directly entered into sample detection cell 22 after being separated in turn. The Sample components flow out the sample detection cell outlet 34 after being detected in turn.

Figure 4:
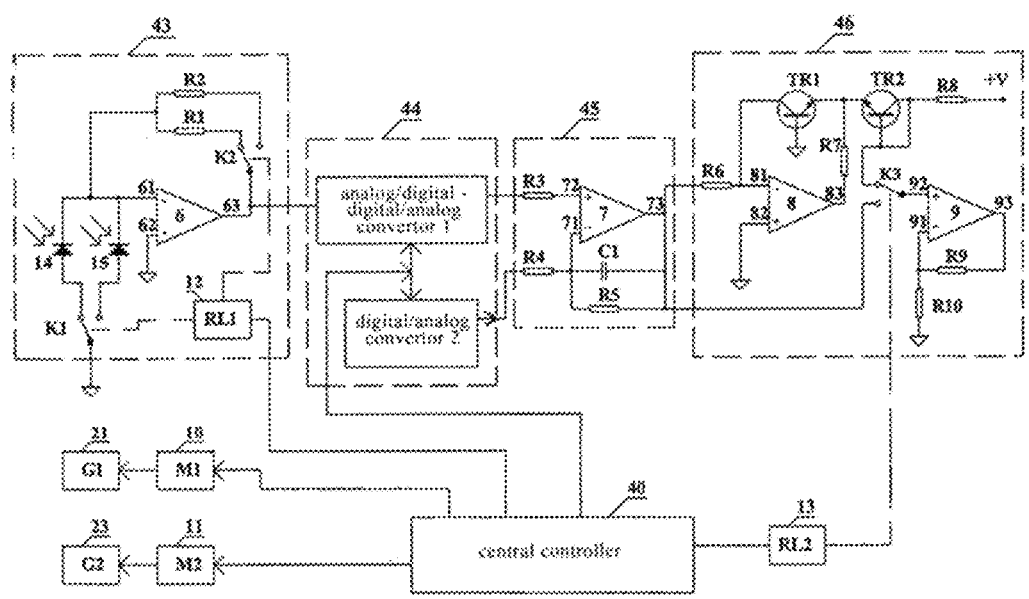
FIG. 4 is a circuit diagram of the electrical work of FIG. 2.
Figure 5:
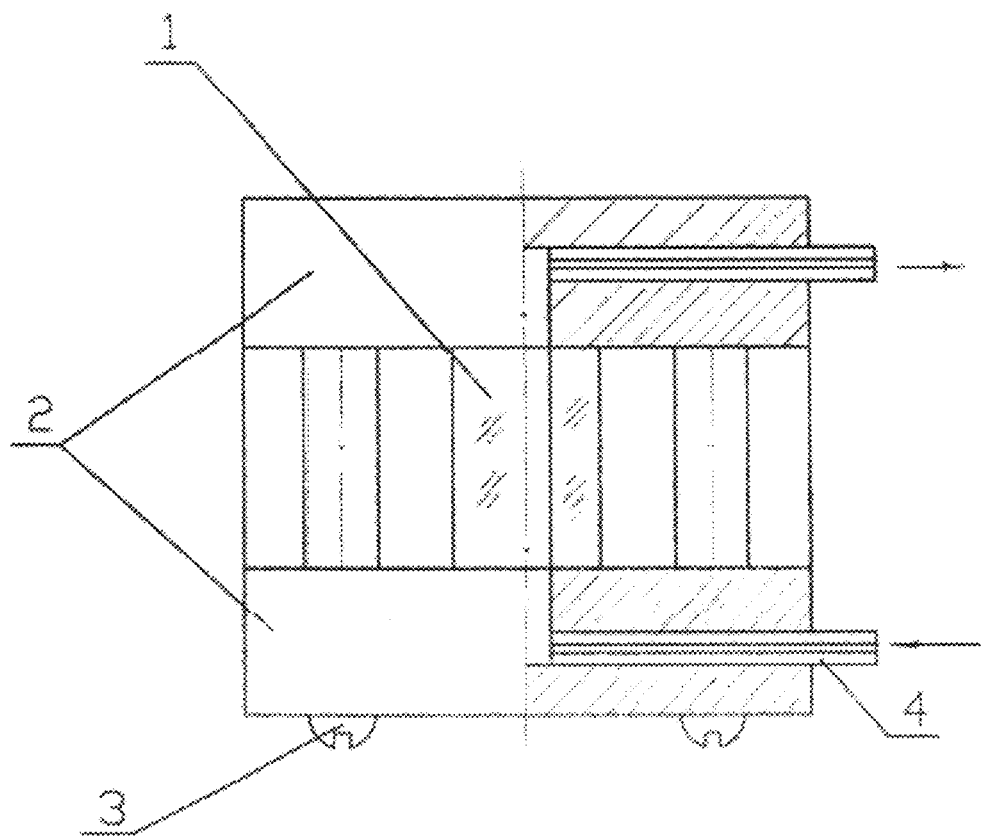
FIG. 5 is a structural diagram of sample detection cells of the present invention.

Specifically, as shown in FIG. 4, the said preposed amplifying module 43 further includes a first resistance R1, a second resistance R2, the shift switch K1 and K2 of the first relay 12, a first photosensitive diode 14 and a second photosensitive diode 15. The first inverting input terminal 61 of the said first operational amplifier 6 is connected with the first and second photosensitive diode 14 and 15 whose negative terminals are connected in parallel, and the first in-phase input terminal 62 is earthed. One terminal of the said first resistance R1 is connected in parallel with that of the second resistance R2 and connected with the first inverting output terminal 61 of the first operational amplifier; the positive terminals of the first and second photosensitive diode 14 and 15 are connected with the shift changeable heads of the first shift switch K1 started by the first relay 12; similarly, the other terminals of the first and second resistance R1 and R2 connected in parallel are connected with the shift changeable heads of the second switch K2 derived by the first relay 12. The said central controller 40 directly controls the first relay 12, so that the normally closed head of the synchronized two shift switches K1 and K2 of the first relay 12 is for ultraviolet detection, and the other normally opened head is for fluorescence detection.

When the preposed amplifying module 43 is working, fluorescence detection is the extremely weak photoelectric signal of the indirect secondary emission wavelength, which is far lower than the photoelectric signals generated during ultraviolet detection by about 4~5 orders of magnitudes, which is a basic reason that high performance double monochromatic fluorescence detector said in the background of the invention is rarely seen in the world. As it is not difficult to amplify the extremely weak photoelectric signals, but it is hard to simultaneously amplify signals, noise, and drift while signal-to-noise ratio is fixed, which leads to the failure in improving the sensitivity and stability, namely, the exclusion and contradiction of sensitivity and stability. For these reasons, the present invention is aimed to solve the objectively existing technical difficulty, and the only method to solve this difficulty is: the most reasonable position in the later mentioned noise processing module 45 to eliminate photoelectric components and pre-stage noise and drift of the instrument has been perfectly solved. The preposed amplifying module 43 is used to convert and amplify the photocurrent signals I14 generated by the ultraviolet first photosensitive diode 14 into voltage signals V=I14×R1. Similarly, the photocurrent signals I15 generated by the fluorescence second photosensitive diode 15 are converted and amplified into voltage signals V=I15×R2 which is output through the first output terminal 63.

Preferably, the said first operational amplifier 6 is high-impedance and low-drift operational amplifier.

Preferably, as shown in FIG. 4, the said auto gain module 44 includes analog/digital-digital/analog convertor 1 and digital/analog convertor 2. The said auto gain module 44 is used due to the difference between ultraviolet detection and fluorescence detection. In the state of mobile phase before sample is entered, when fluorescence detection key F is pressed to conduct fluorescence detection, the second photosensitive diode 15 is just a low background in which non-luminous dark current with little incidence is used as the instrument baseline. As the photoelectric current of fluorescence emission wavelength, which is generated after sample is entered, is larger than dark current, the chromatographic diagram is generated in which various components of samples are converted into voltage detection signals; but when ultraviolet detection key U is pressed to conduct ultraviolet detection, there are two special aspects different from other detectors: first, the first photosensitive diode 14 is in a state of mobile phase with very small absorption, and it is a high background in which the largest photoelectric current generated by the incidence of all optical energy is used as the instrument's baseline; second, after sample is entered, it is absorbed in accordance with Beer's Law:

Absorption unit AU=LOG incidence photoelectric signal/transmission photoelectric signal=absorption coefficient×sample concentration (after logarithm)

Due to the absorption of samples, transmission photoelectric signal of denominator are all smaller than initial incidence photoelectric signals of mobile phase; Due to the spectrum characteristics of the three major optical components: light source L, raster G1, G2 of monochromatic spectroscopic device and receiving photosensitive diode PD1 and PD2, namely, the relationship between y-coordinate (photoelectric current/voltage) and x-coordinate (optical wavelength) varies according to different wavelengths, and the optical current/voltage differs greatly. And such phenomenon makes one of the three physical parameters in Beer-Lambert Law unknown (transmission photoelectric signal), one variable (incidence photoelectric signal), and technical targets of only one optical wavelength can be calculated, calibrated, inspected, and tested: noise and drift, (general steps are as follows: test the voltage value of incidence light of this wavelength-set the absorption unit AU value first-use the logarithm table to evaluate the theoretical voltage value of transmission light according to the set AU value-then do the practical test and prove the correct value of y-coordinate voltage of chromatogram corresponding to AU value: specific method is to get the summation of the voltage value of the input terminal of logarithm amplifying module plus the difference between incidence light voltage and theoretical voltage value of transmission light that has been evaluated after the set of AU value—i.e. logarithm computation formula that meets the said law—evaluate the output voltage tested in the output terminal of logarithm amplifying module, namely, the correct output voltage and absorption unit AU value evaluated in inverse method—thus based on the uniform rules evaluate: noise=1% AU value; drift=10 times noise AU/hour). The observation of calculation steps of Beer Lambert Law, especially the requirements to meet Beer Lambert Law causes the following two difficult problems: first, the incidence photoelectric signal, which is the right numerator of Beer Lambert Law, is different from each other in every wavelength, and the AU value of every corresponding wavelength is different too. Thus, the noise and drift calculated is different in every wavelength as well. For products without the auto gain technology, it will be tedious and difficult to calculate, calibrate, inspect and test hundreds of wavelengths; therefore, it is the basic reason for incomplete technical targets and failure in calculating, calibrating, inspecting, and testing the whole wavelength technical targets with existing ultraviolet detectors. Second, weakness of light energy of three optical devices like light source due to increase in service time will lead to the change in incidence photoelectric signal and absorption unit AU value, and it is impossible to re-calibrate various parameters of instruments that have been sold, which will cause the inaccuracy of the correct value that has been calibrated originally. As a result, as said in the background of the invention—all the existing ultraviolet products can only get technical targets of only one wavelength (which becomes inaccurate along with the service time), and cannot calculate, calibrate, inspect, and test the AU value, noise value, and drift value of other hundreds of wavelengths correctly. To overcome and solve the objectively existing technical problem, the only way is to keep the right numerator in Beer Lambert Law: the incidence photoelectric signal of various wavelengths constant (namely, the necessity of auto gain). In this way, only one calibration can solve the correct calibration of various wavelengths in the whole wavelength range and can be revised any time. Therefore, it can remain accurate over time. What is more practicable is that it facilitates the accuracy of directly inspecting and testing noise and drift technical targets from voltage value corresponding to y-coordinate AU value of experimental chromatogram. To realize this purpose, the present invention has the specific embodiment that auto gain module 44 controls every wavelength in the whole wavelength range to the necessary amplifying or subtracting times, thus to realize the constant voltage in the output terminal of analog/digital-digital/analog convertor 1;

Specific operation: during ultraviolet detection, select a three-digit number of the commonly used analysis wavelength first, and then press the wavelength confirmation key of the control keyboard 32 to reach the accurate analysis wavelength. After the auto gain key is pressed, the voltage signal of the first output terminal 63 of the preposed amplifier are converted into digital signals in the analog/digital-digital/analog convertor 1 by the said central controller 40 which controls the amplifying or subtracting of the digital signals in analog/digital-digital/analog convertor 1 (namely, the increase or reduction of pulse), until the voltage of the output terminal of analog/digital-digital/analog convertor 1 reaches the designed constant value, and then the increase or reduction of pulse is stopped; later, when the analysis wavelength is changed, according to the said steps, central controller 40 controls different voltage signals generated by different wavelengths in the first output terminal 63 in analog/digital-digital/analog convertor 1, and keeps the voltage of the output terminal of analog/digital-digital/analog convertor 1 constant when the wavelength is changed every time, to realize the purpose of auto gain;

Further, as shown in FIG. 4, the said noise processing module 45 still includes the third resistance, the fourth resistance R4, and the fifth resistance R5 and the first capacitor C1. The second in-phase input terminal 72 of the said second operational amplifier 7 is connected with the output terminal of analog/digital-digital/analog convertor 1 through the third resistance R3, and the second inverting input terminal 71 of the second operational amplifier is connected with the output terminal of the digital/analog convertor 2 through the fourth resistance R4. One terminal of the said fifth resistance R5 is connected with the second inverting input terminal 71, and the other one is connected with the second output terminal 73. The said first capacitor C1 is connected with the fifth resistance R5 in parallel, and the first capacitor C1 can eliminate high-frequency noise in voltage of the second output terminal 73. The second output terminal 73 of the second operational amplifier 7 is connected with the input terminal of logarithm amplifying module 46. Specific methods: use the central controller 40 to conduct determining to analog/digital-digital/analog convertor 1 separately in a static state in advance. As long as there is an adjustable constant voltage value accessed from outside to be input into the input terminal of analog/digital-digital/analog convertor 1 and at the same time it is equivalent to that designed by auto gain, i.e. the output terminal of auto gain module can also reach the designed constant voltage through 1:1 digital and analog operation. Then the central controller 40 can determine the stable value of digital signals of the analog/digital-digital/analog convertor 1, i.e. constant static digital signal. The central controller 40 also controls digital/analog convertor 2 to deposit stable digital signals of analog/digital-digital/analog convertor 1, and when the instrument is started and operates dynamically, the sample detection voltage of the first output terminal 63 of the preposed amplifier also includes dynamical variable noise and drift value Vn of the instrument generated by mobile phase, photoelectric devices and the first operational amplifier, which is converted into digital signals in analog/digital-digital/analog convertor 1 randomly by central controller 40 composed of microcomputers. And for the said purpose of auto gain, digital amplifying or subtracting have to be adopted so that the output terminal of analog/digital-digital/analog convertor 1 can reach the designed constant voltage value, while the said dynamic variable value Vn is also included. To eliminate this unstable part, first, use the central controller 40 to execute the subtraction between digital signals of the random dynamic and static state of digital/analog convertor 1 and 2 in digital/analog convertor 2. Then obtain the variable value Vn of noise and drift of the instrument only generated between the dynamic and static state in the output terminal of digital/analog convertor 2. After then, transmit the voltage signal Vn to the second inverting input 71 of the second operational amplifier 7 randomly through the fourth resistance R4 simultaneously so that it can offset the instrument's dynamic noise and drift variation value Vn which is input to the second in-phase input by output terminal of analog/digital-digital/analog convertor 1, to realize the random tracing, operation, and noise processing of the instant variable signals in a small range, so as to maintain the stable and constant voltage value of the voltage signals of the second output terminal 73 of the noise processing module 45 and therefore when the noise is eliminated, the drift is reduced as well. And when various components of samples are entered, only the voltage signal of the initial Vn of mobile phase is offset, while the voltage signals of sample components larger than Vn are amplified and output through the logarithm processing of the logarithm amplifying module 46. The long-term objectively existing technical difficulties are overcome and solved in the noise processing module 45: as aforesaid, the voltage signals of various sample components and the unstable and invalid instrument's noise and drift are amplified simultaneously, which causes that signal-to-noise ratio does not change. The only effective way is to use dual-purpose technology of eliminating a lot of noise and drift (i.e. improving the stability) for both ultraviolet and fluorescence detector in the said invention. Therefore, more amplifying can be implemented in both the front and back modules, and sensitivity is greatly improved when the stability is enhanced. Thus the objectively existing worldwide technical difficulty of mutual exclusion and contradiction of sensitivity and stability is perfectly solved, and the extremely high sensitivity, stability, and accuracy of detection and analysis results are guaranteed.

Further, as shown in FIG. 4, the said logarithm amplifying module 46 includes the third and fourth operational amplifier 8 and 9, double transistors Tr1 and Tr2, resistance R6, R7, R8, R9 and R10; the specific operation: the central controller 40 conducts the following execution to the stable voltage signals output by the noise processing module 45 respectively through shift switches: when the ultraviolet set key U is pressed and the shift switch K3 is the normally closed head, ultraviolet detection is conducted and the amplifying is carried out after logarithmic transformation according to the said Beer Lambert Law. According to the theoretical and practical test of transistor when the base electrode is earthed and Vc=0, collector electrode current Ic has an exponential relationship with emission electrode voltage Ve, i.e. Ic=K×expVe. And the collector electrode of transistor Tr1 is connected with the inverting input terminal 81 of the operational amplifier 8, which can meet the condition of Vc=0, and the emission electrode of this transistor is connected with the output terminal 83 of the operational amplifier 8 through R7. Therefore, after the logarithm is taken from both sides of the formula, voltage Ve of the emission electrode has a linear relationship with the logarithm of the input current through which the stable voltage of the second output terminal 73 divides by the sixth resistance R6 (namely, the collector electrode current Ic). Due to the processing in auto gain module 44, the voltage signal in numerator of Beer Lamber Law becomes a stable constant (i.e. the constant that does not change with the wavelengths even when the logarithm is taken), and only the denominator changes with the voltage of different wavelengths from which the logarithm is taken to the samples different absorption after the sample is entered. The numerator equals the denominator in the dynamic condition that the mobile phase flows stably before the sample is entered. Therefore, absorption unit AU value on the left side of Beer Lambert Law is zero. To conform to the said theory, the setting on the electrical circuit: the collector electrode of transistor Tr2 is connected with the base electrode, and is also connected with stable direct voltage +V (equivalent to constant voltage value which is designed by auto gain) through the eighth resistance R8. As the emission electrodes of Tr1 and Tr2 are connected, the voltage which is input to the in-phase input terminal 92 of the ninth operational amplifier 9 equals to the difference value after logarithms are taken from the numerator and the denominator on the right side of Beer Lambert Law. The theoretical and practical requirements can be met as long as the eighth resistance R8 or direct voltage +V is adjusted a little, i.e. the voltage of this output terminal should be zero before the sample is entered. The seventh resistance R7 is used to protect the operational amplifier 8 and the transistor Tr1 which makes logarithm, to avoid overloading: after the logarithm processing is finished, amplifying of voltage signals is realized through the operational amplifier 9, the ninth resistance R9, and the tenth resistance R10, with the amplifying multiple K=R9+R10/R10. When the analysis takes a long time, especially in the condition that repeatability of quantitative analysis is required to be good, and a trace amount of baselines deviating zero are generated, press the automatically zero set key, and then enter sample solution after the central controller 40 automatically controls analog/digital-digital/analog convertor 1 to make the voltage of output terminal equal to the baseline of zero; when the fluorescence set key F is pressed and the shift switch K3 is a normally opened contact, then central controller 40 conducts the switch of the shift switch K3 of the second relay 13, and no logarithm processing is needed. The amplifying is conducted directly by the operational amplifier 9 from the second output terminal 73 of the noise processing module 45. Two detectors respectively transfer voltage signals to the output interface 35 of detection signals through the fourth output terminal 93, and then transmit them to the chromatography data work-station. The processed analysis results are displayed as chromatogram on the display screen of the connected computer, and the analysis chromatogram and data can be saved and printed.

In conclusion, the present invention relates to the both ultraviolet-visible and double monochromatic fluorescence dual detector, which can be used for detecting various ultraviolet-visible wavelengths as well as high-grade double monochromatic fluorescence. An artful structure design is adopted. And light path of only single light source (it is the first time to use deuterium lamp as the light source for fluorescence detection in the field of liquid chromatography), single sample detection cell and single set of electrical circuit are used to realize detection and analysis functions of two detectors. To overcome the ubiquitous problem of ultraviolet-visible detector's incomplete technical targets which exists in current technologies and the difficulty in calculating, calibrating, inspecting and testing main technical targets of noise and drift of other hundreds of wavelengths, the present invention adopts the auto gain technology that can solve the problem, to quickly and effectively achieve the complete targets within the whole wavelength range during ultraviolet-visible detection, and to correctly calculate, calibrate, inspect and test technical targets of each wavelength; besides that digital signal amplifying and subtracting is controlled by digital/analog convertor in an auto gain way as said above, photomultiplier has been also successfully adopted as the photoelectrical receiving device and the direct control of the increase or reduction of negative high voltage of photomultiplier can realize the auto gain purpose of analog photoelectrical signals; further, both theory and practice have proved that the said auto gain technology can only solve the problem of incomplete technical targets, but cannot solve the worldwide difficulty to effectively improve signal-to-noise ratio so as to enhance technical performance. To overcome problems that sensitivity and stability cannot be improved effectively (i.e. signal-to-noise ratio cannot be improved greatly) which exist in all the current ultraviolet-visible detector and the rare high-grade double monochromatic fluorescence detector, the present invention also adopts an innovative dual techniques that can automatically eliminate noise and reduce drift of the instrument at the same time, so that the "one instrument for dual purpose" can be realized. Moreover, the worldwide technological problem of sensitivity-stability exclusion and contradiction that objectively exists in ultraviolet and fluorescence detectors is solved with the sensitivity and stability greatly improved, to ensure the remarkable technical innovation, advancement, and practicability of the instrument.

Embodiments in which the invention is used to detect different sample components are listed:

Embodiment 1

Ultraviolet-visible detection is applied in the present invention:

Analysis wavelength: FIG. above: 210 NM, FIG. below: 254 NM

Figure 6:
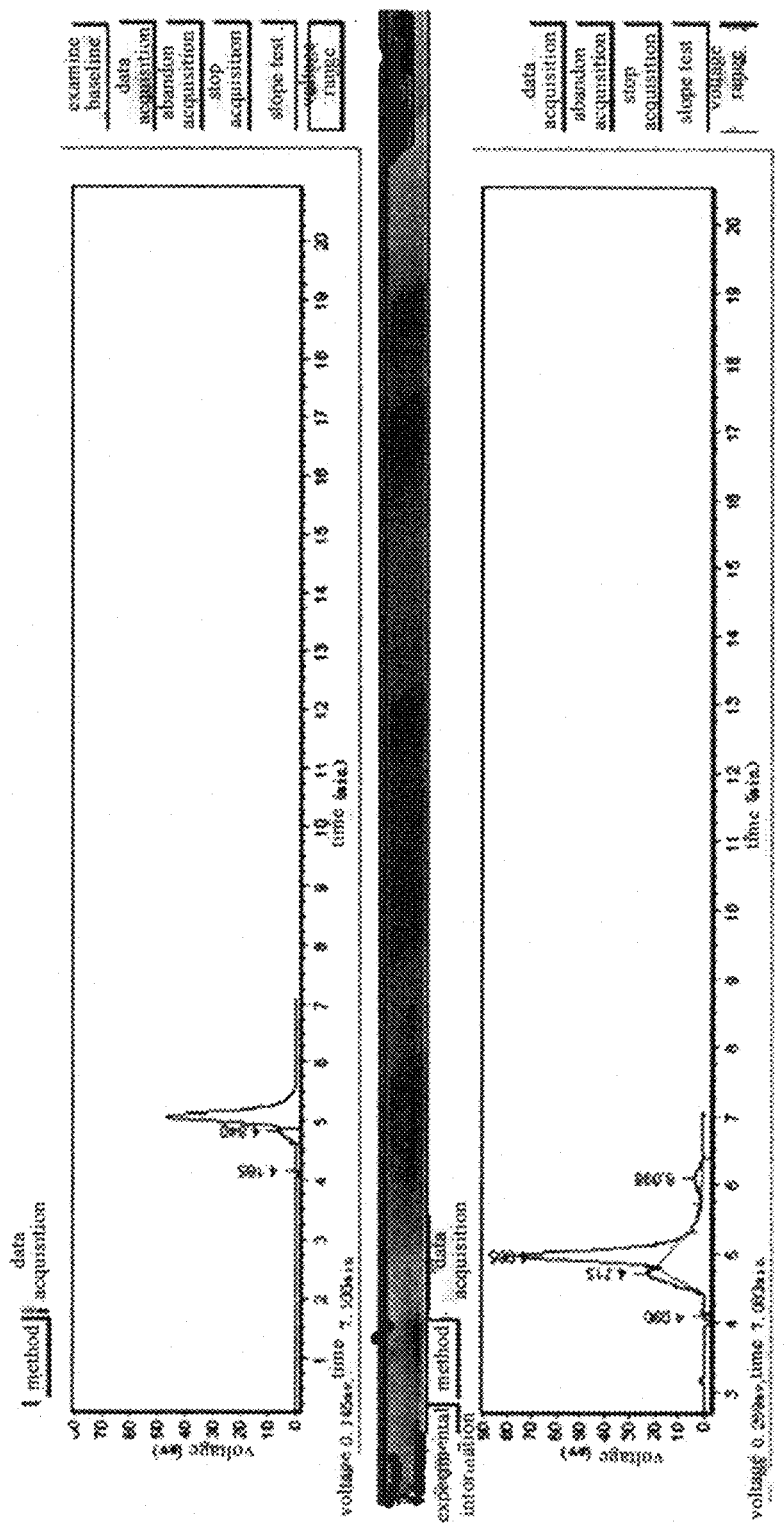
FIGS. 6-19 are chromatograms obtained by using the detector to detect the components of a sample.

Detection sample: naphthalene (standard detection sample of ultraviolet detector), calculation result: the minimum detection concentration better than 5 nanogram/ml; Noise: better than 4 micro AU; Drift: better than 40 micro AU/hour Detection environment: chromatographic column: C18; mobile phase: 100% methyl alcohol; flow velocity: 1 ml/min Chromatogram obtained after the detection is as shown in FIG. 6.

In brief: main technical targets detected practically: the minimum detection concentration, noise, and drift are 10 times better than the standard. 210 NM wavelength is the worst wavelength interval of sensitivity and stability of all similar products. From the chromatogram, it can be seen that the product can realize the excellent sensitivity and stability in the whole wavelength range after using the innovative art of the present invention; in the meanwhile, 210 NM and 254 NM have sensitive absorption chromatographic peak signals for the same sample (naphthalene sample in the embodiment), which shows the false high sensitivity and other technical errors that go against Beer Lambert Law for the "DAD diode array ultraviolet detector" which adopts hybrid light of various incidence wavelengths into sample detection cell.

Embodiment 2

Ultraviolet-visible detection is applied in the present invention: Analysis wavelength: 325 NM Detection sample: vitamin A (sample that should be detected in the milk according to standards)

Figure 7:
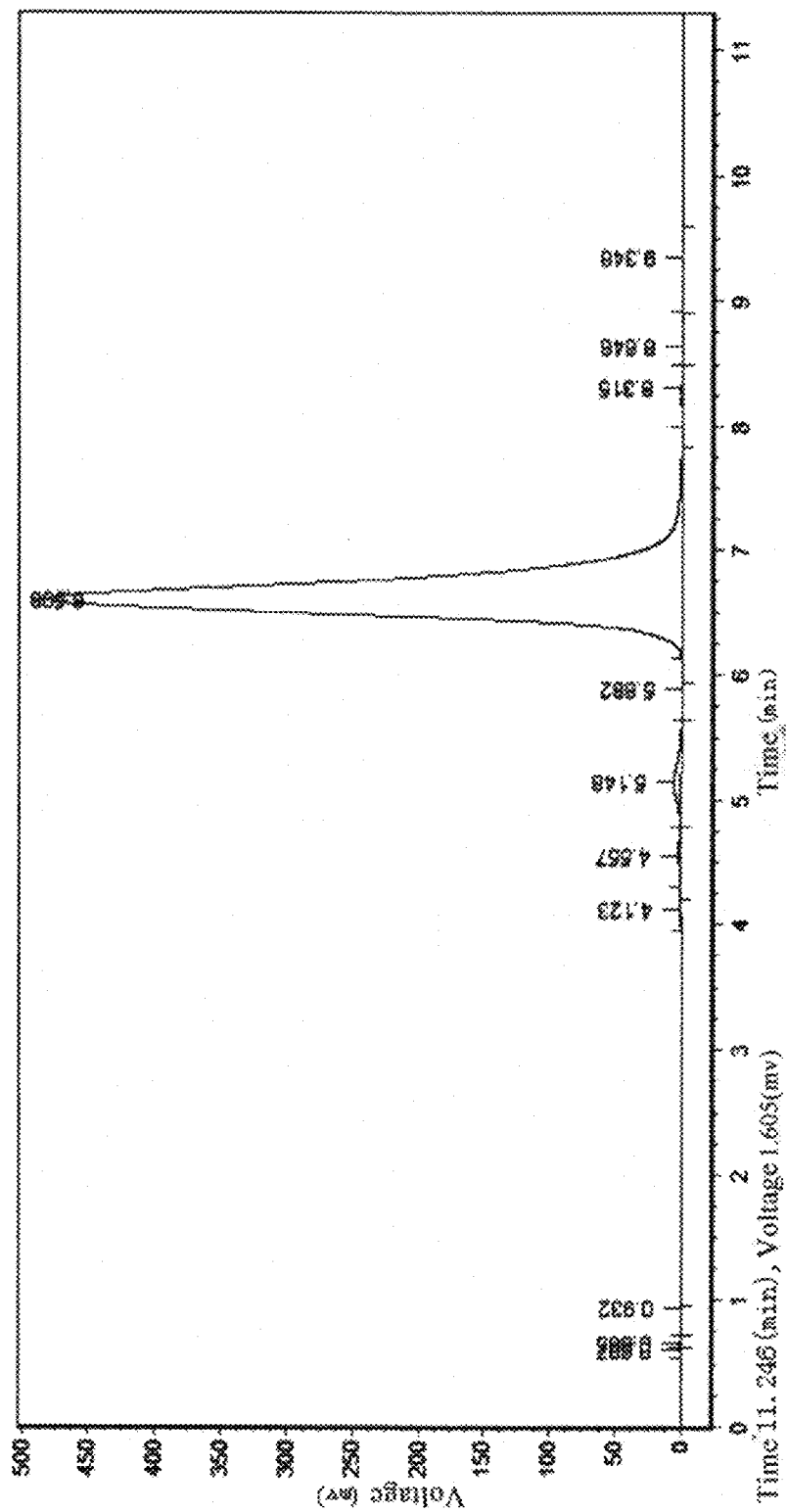

Detection environment: chromatographic column: C18; mobile phase: 100% methyl alcohol; flow velocity: 1 ml/min Chromatogram obtained after the detection is as shown in FIG. 7.

In brief: milk is a daily drink for nutrition, containing vitamin A whose content in the milk cannot be detected easily as existing products have general sensitivity and poor stability.

Embodiment 3

Ultraviolet-visible detection is applied in the present invention:

Analysis wavelength: 245 NM

Detection sample: melamine (sample that should be detected in the milk according to standards)

Figure 8:
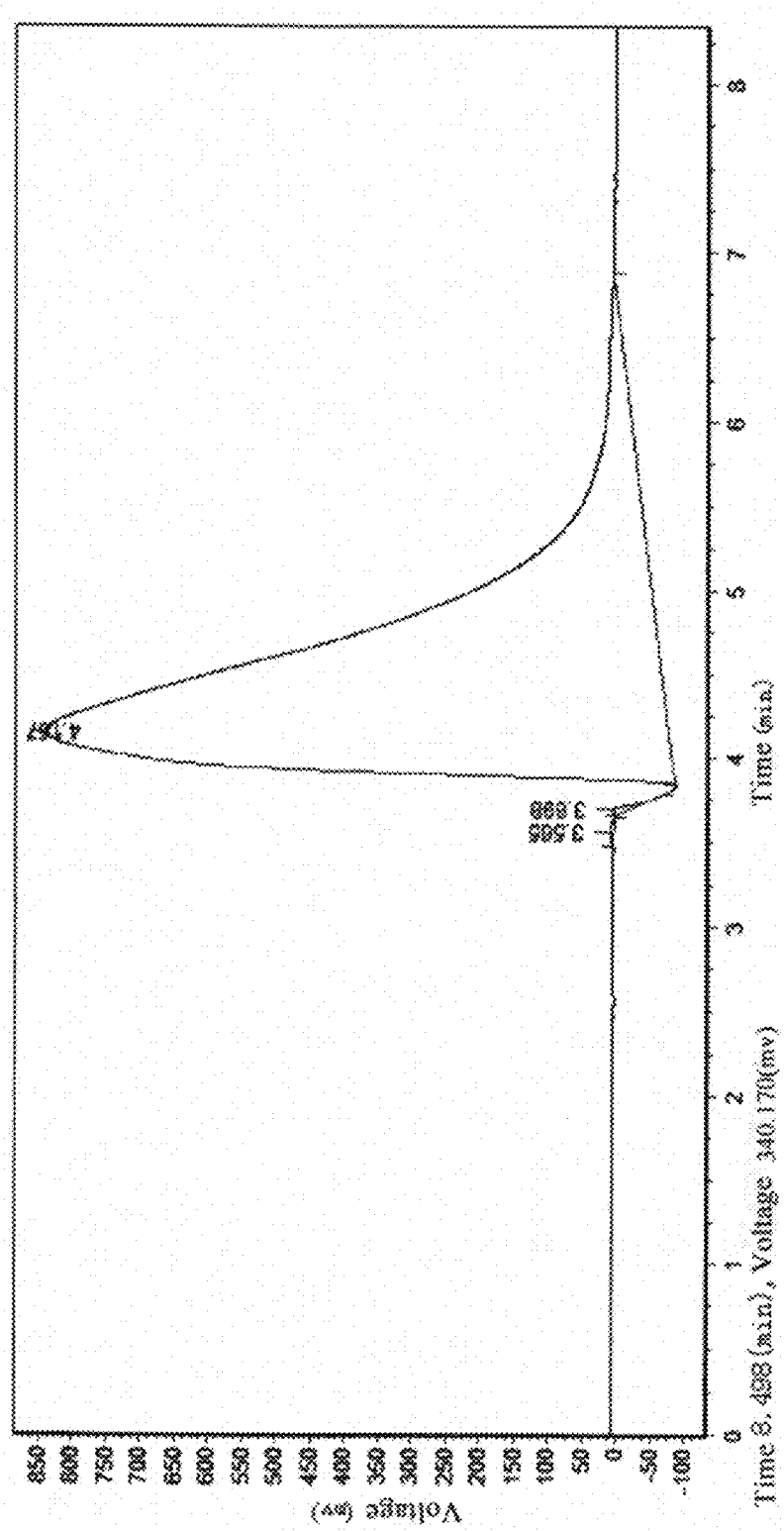

Detection environment: chromatographic column: C18; mobile phase: 100% methyl alcohol; flow velocity: 1 ml/min Chromatogram obtained after the detection is as shown in FIG. 8.

In brief: melamine is a harmful substance mixed into the milk to improve the false content of protein. Though the detection can be conducted with simple detection test, shapes of chromatographic peak will be a little distorted.

Embodiment 4

Fluorescence double spectroscopical detection is applied in the present invention: excitation wavelength: 345 NM, emission wavelength: 455 NM Detection sample: quinine sulfate/perchloric acid water solution (sample that should be detected in the fluorescence detector according to standards); sample concentration: 1 nanogram/ml Calculation result: the minimum detection concentration is better than 10 micromicrogram/ml;

Noise: better than 0.01 FU; Drift: better than 0.1 FU/hour

Figure 9:
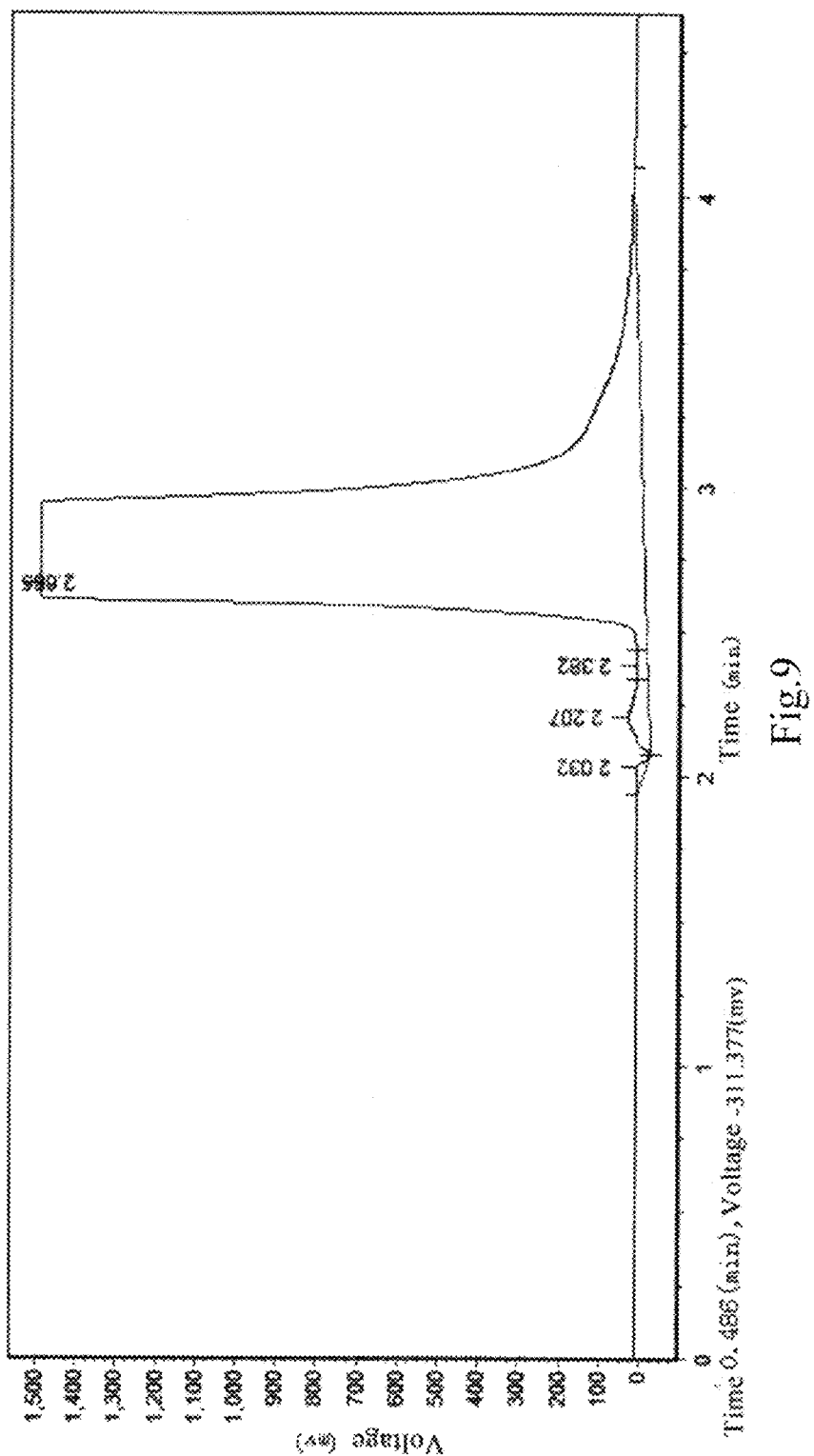

Detection environment: chromatographic column: C18; mobile phase: 85% methyl alcohol/water solution; flow velocity: 1 ml/min Chromatogram obtained after the detection is as shown in FIG. 9.

In brief: fluorescence detection of HPLC is much more difficult than that of fluorescence spectrophotometer of the laboratory, because of the extremely small volume of sample detection cell and transmission aperture less than 2 mm. It is difficult to excite the sample to generate fluorescence of secondary emission wavelength and extremely weak signal of secondary emission fluorescence, leading to very small signal-to-noise ratio that needs to be amplified a lot. However, stability including noise and drift is amplified randomly together, limiting the improvement of sensitivity. It is the main reason why such high grade products are rarely seen abroad. The present invention adopts double technology to automatically eliminate noise and reduce drift at the same time, which realizes excellent stability and the extremely high sensitivity more than 100 times higher than standards.

Embodiment 5

Figure 10:
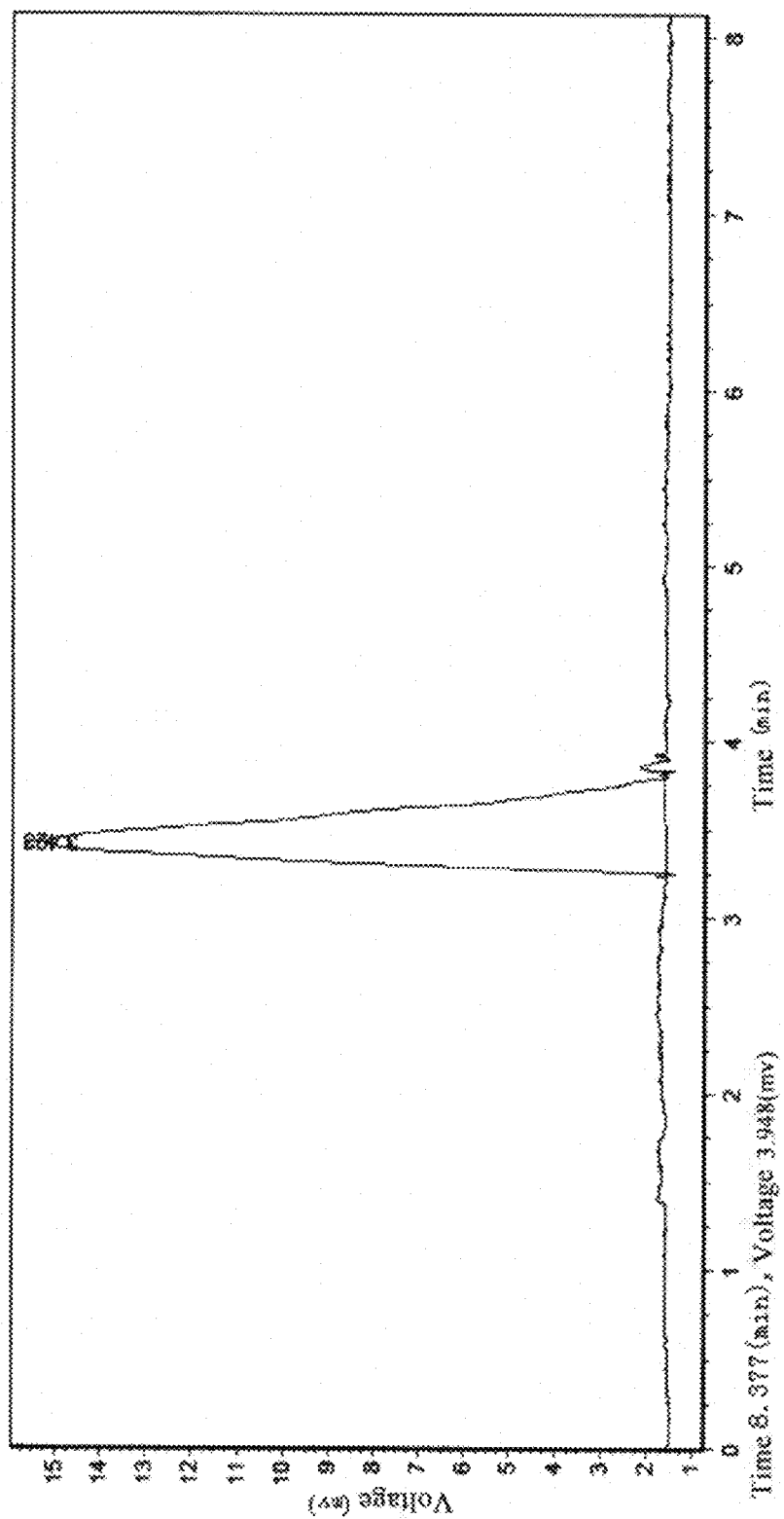

Fluorescence double spectroscopical detection is applied in the present invention: excitation wavelength: 375 NM, emission wavelength: 435 NM Detection sample: vitamin B1 (sample that should be detected in the milk according to standards);

Detection environment: chromatographic column: C18; mobile phase: 35% methyl alcohol/trichloroacetic acid sodium water solution; flow velocity: 1 ml/min Chromatogram obtained after the detection is as shown in FIG. 10.

In brief: fluorescence detector of HPLC can detect vitamin B1 contained in the milk. However, as there are not many high performance fluorescence detectors, there are only little application examples of detection.

Embodiment 6

Figure 11:
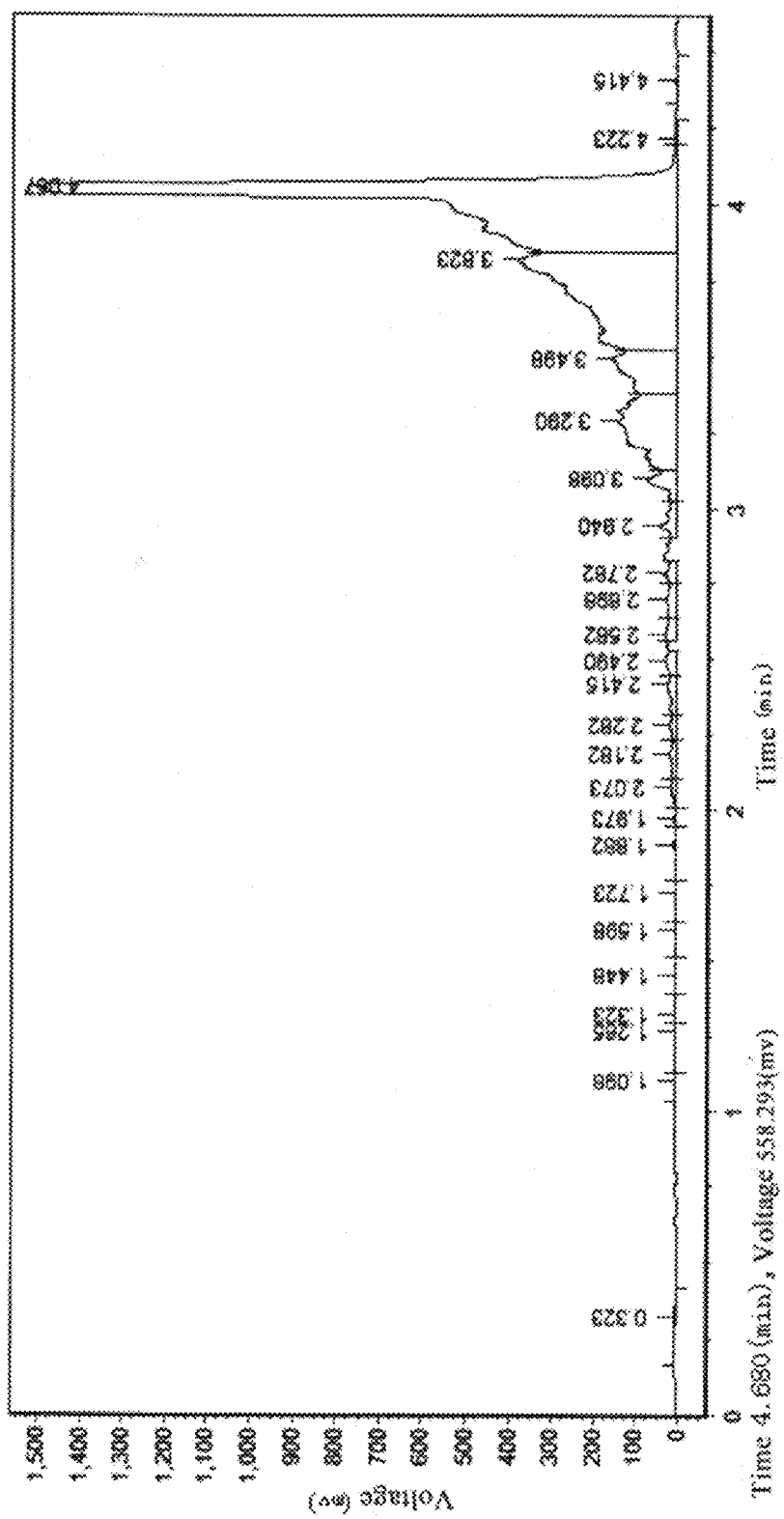

Fluorescence double spectroscopical detection is applied in the present invention: excitation wavelength: 290 NM, emission wavelength: 330 NM Detection sample: naphthalene (sample used to detect wavelength errors of the fluorescence detector according to standards);

Detection environment: chromatographic column: C18; mobile phase: 100% methyl alcohol; flow velocity: 1 ml/min Chromatogram obtained after the detection is as shown in FIG. 11.

In brief: naphthalene sample is used to test wavelength accuracy errors of fluorescence detector and application range of wavelength accuracy can be detected and expanded. Moreover, the ultraviolet wavelength has less energy than the visible wavelength and the excitant is not added with cold excitation, so it is difficult to be excited, and the phenomenon of delayed and slow excitation can be seen in the chromatogram.

Embodiment 7

Ultraviolet-visible detection is applied in the present invention:

Analysis wavelength: 240 NM

Detection sample: traditional Chinese medicinal material: cynomorium songaricum

Figure 12:
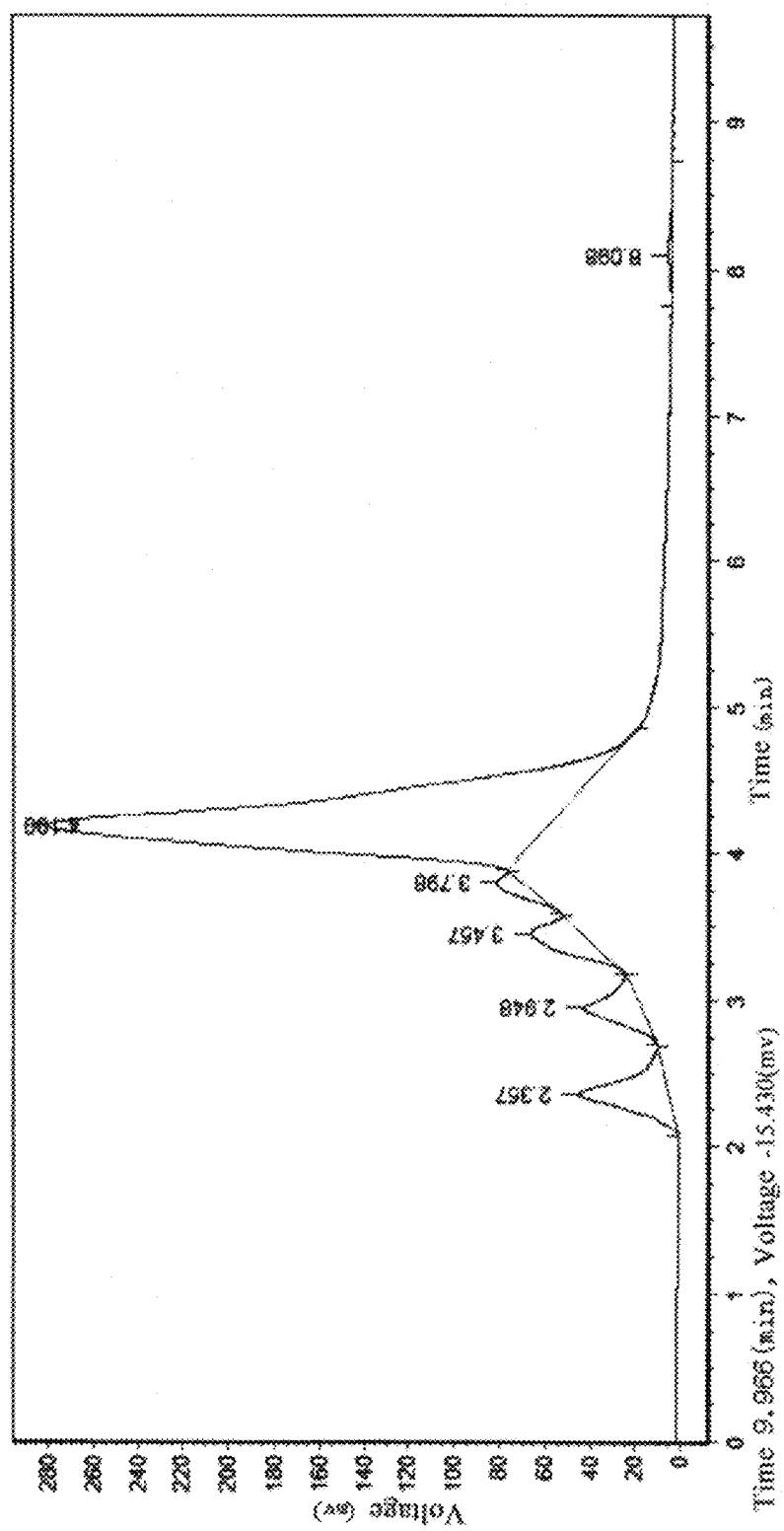

Detection environment: chromatographic column: C18; mobile phase: 100% methyl alcohol; flow velocity: 0.6 ml/min Chromatogram obtained after the detection is as shown in FIG. 12.

In brief: embodiments 7 and 8 are the detection and analysis of ingredients of traditional Chinese medicinal materials, and there are no standards or standard samples. First, the test is conducted to see whether various components can be detected. At the same time, technical performance of the instrument is inspected. It can be seen from this chromatogram that other components are included apart from the main components. In future, better and clearer separation work needs to be done to the small content of small peaks.

Embodiment 8

Ultraviolet-visible detection is applied in the present invention:

Analysis wavelength: 254 NM

Detection sample: traditional Chinese medicinal material: Shenbaoguo

Figure 13:
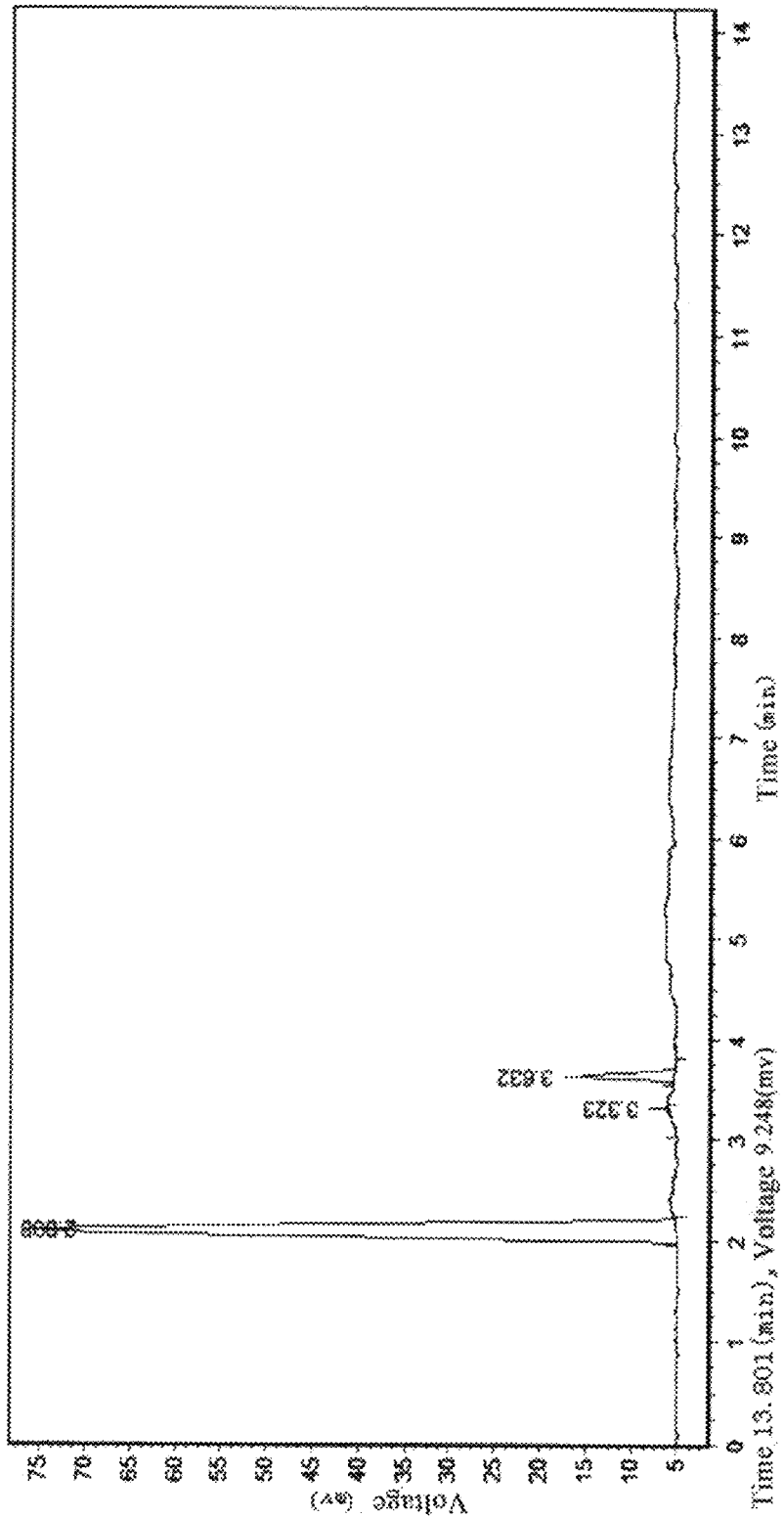

Detection environment: chromatographic column: C18; mobile phase: 100% methyl alcohol; flow velocity: 0.6 ml/min Chromatogram obtained after the detection is as shown in FIG. 13.

Embodiment 9

Ultraviolet-visible detection is applied in the present invention:

Analysis wavelength: 260 NM

Detection sample: health care product: MACA (produced in Peru)

Figure 14:
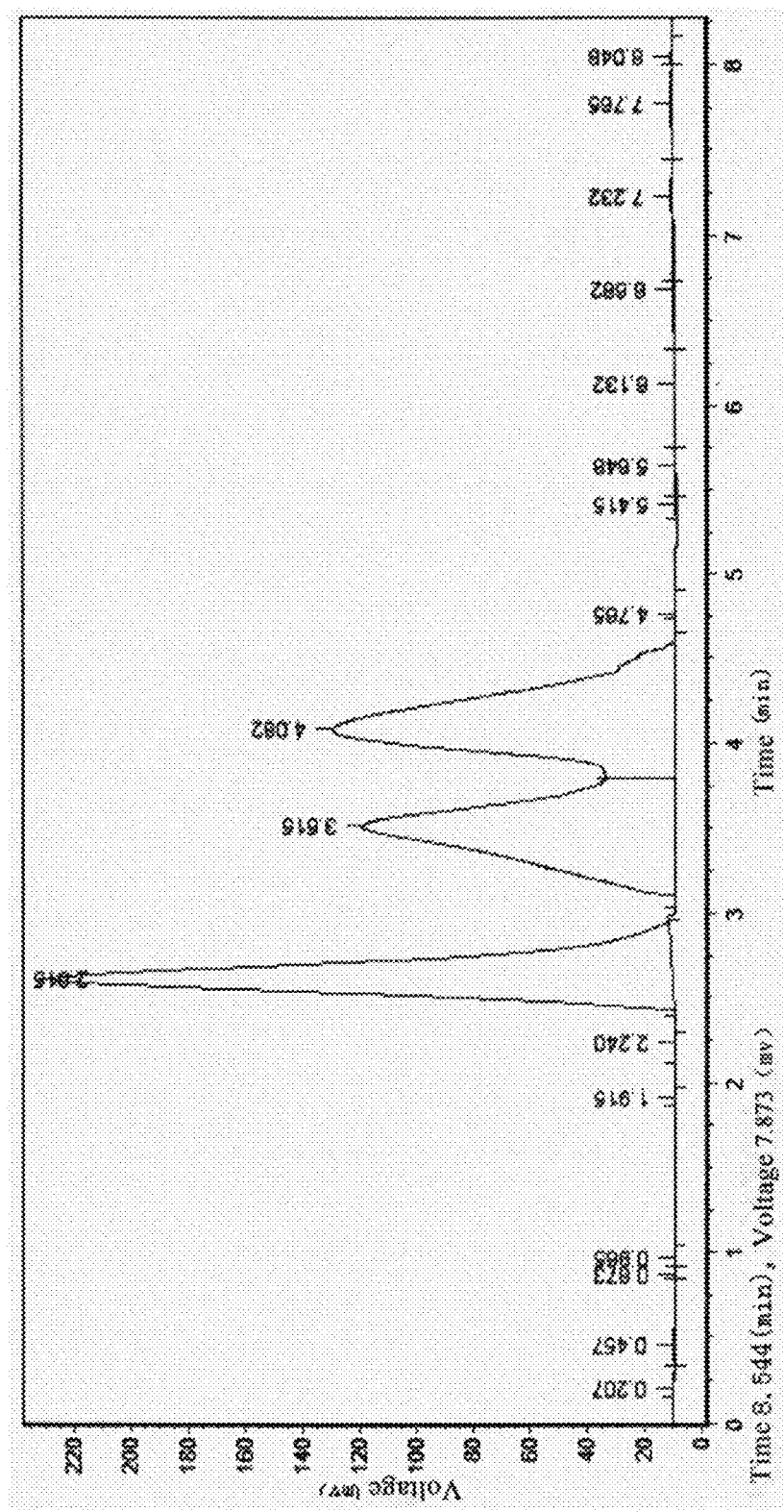

Detection environment: chromatographic column: C18; mobile phase: 100% methyl alcohol; flow velocity: 0.6 ml/min Chromatogram obtained after the detection is as shown in FIG. 14.

In brief: first, it is necessary to know this imported health care product, and the test result shows that at least three components of relatively high content need to be determined qualitatively so that components and function beneficial to health can be known.

Embodiment 10

Ultraviolet-visible detection is applied in the present invention:

Analysis wavelength: 254 NM

Detection sample: natural health care product: *lycium barbarum* (produced in Ningxia of China)

Figure 15:
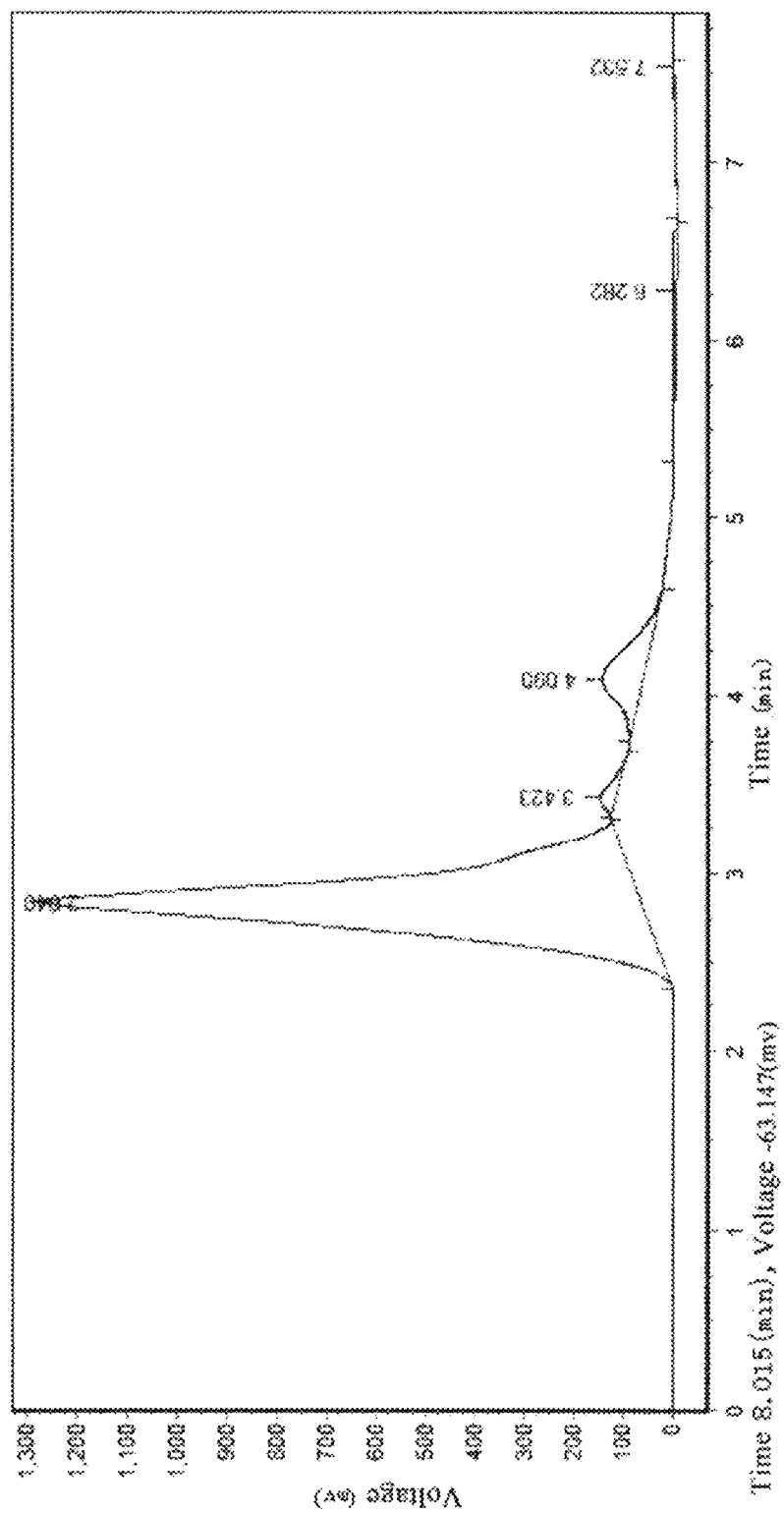

Detection environment: chromatographic column: C18; mobile phase: 100% methyl alcohol; flow velocity: 0.6 ml/min Chromatogram obtained after the detection is as shown in FIG. 15.

In brief: *lycium barbarum* is a commonly used health care and medical product. The chromatogram can show that apart from the main peak of high content, at least another two components of low content are included.

Embodiment 11

Figure 16:
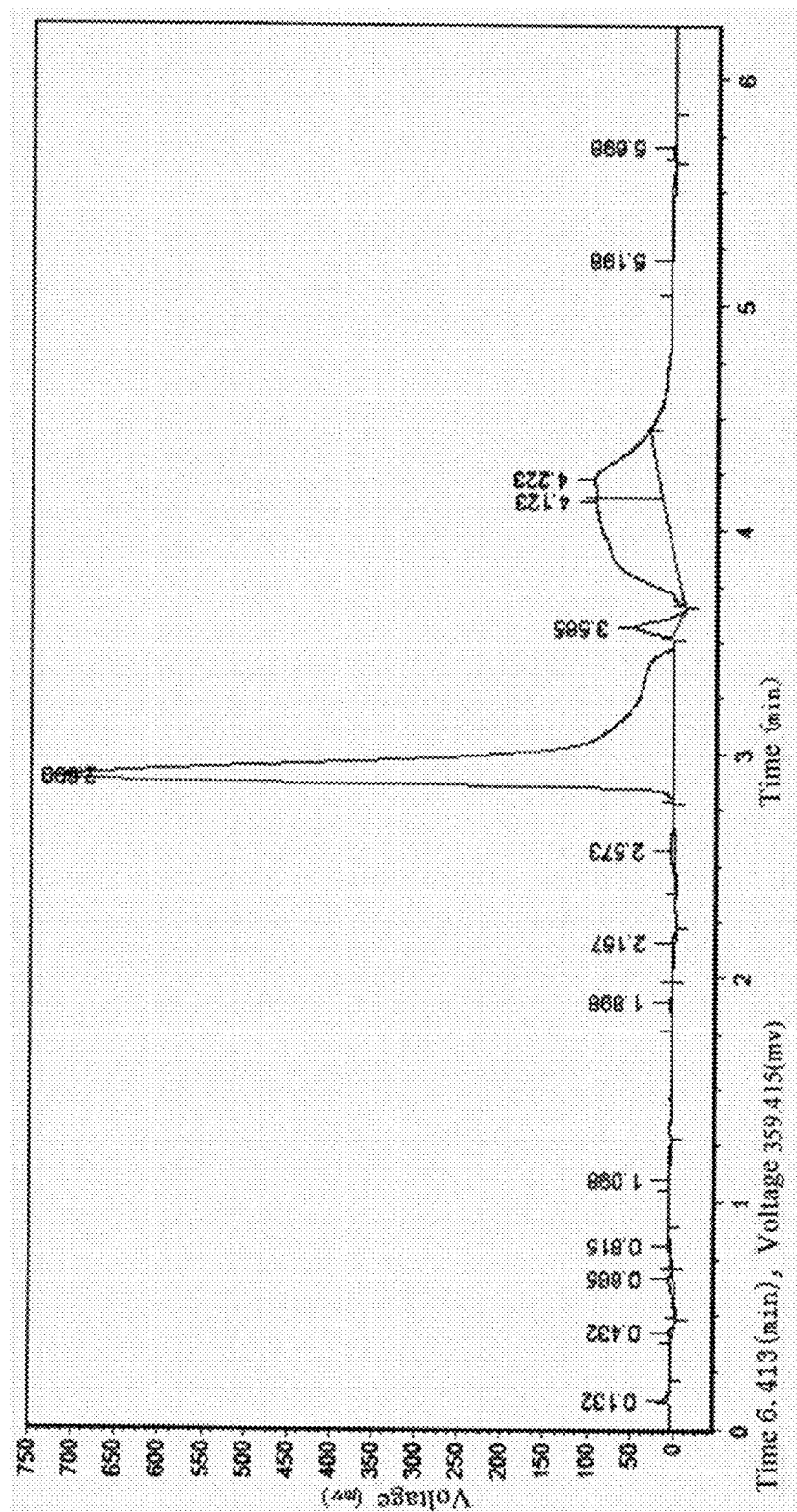

Ultraviolet-visible detection is applied in the present invention:
Analysis wavelength: 258 NM
Detection sample: Yili pure milk
Detection environment: chromatographic column: C18; mobile phase: 100% methyl alcohol; flow velocity: 0.6 ml/min
Chromatogram obtained after the detection is as shown in FIG. 16.

In brief: this embodiment 11 and the following embodiments 12, 13 and 14 are aimed to test whether the drinks, seasoning, and life products can be detected by the instrument. Repeated tests and comparison can be conducted to the same sample, general rules of high or low quality can be told, and it is conducive to the quality protection and food and medicine safety; this chromatogram shows one main component. Some of the low-content components are separated while some are not separated clearly. Test of main content can inspect the quality difference of the milk.

Embodiment 12

Figure 17:
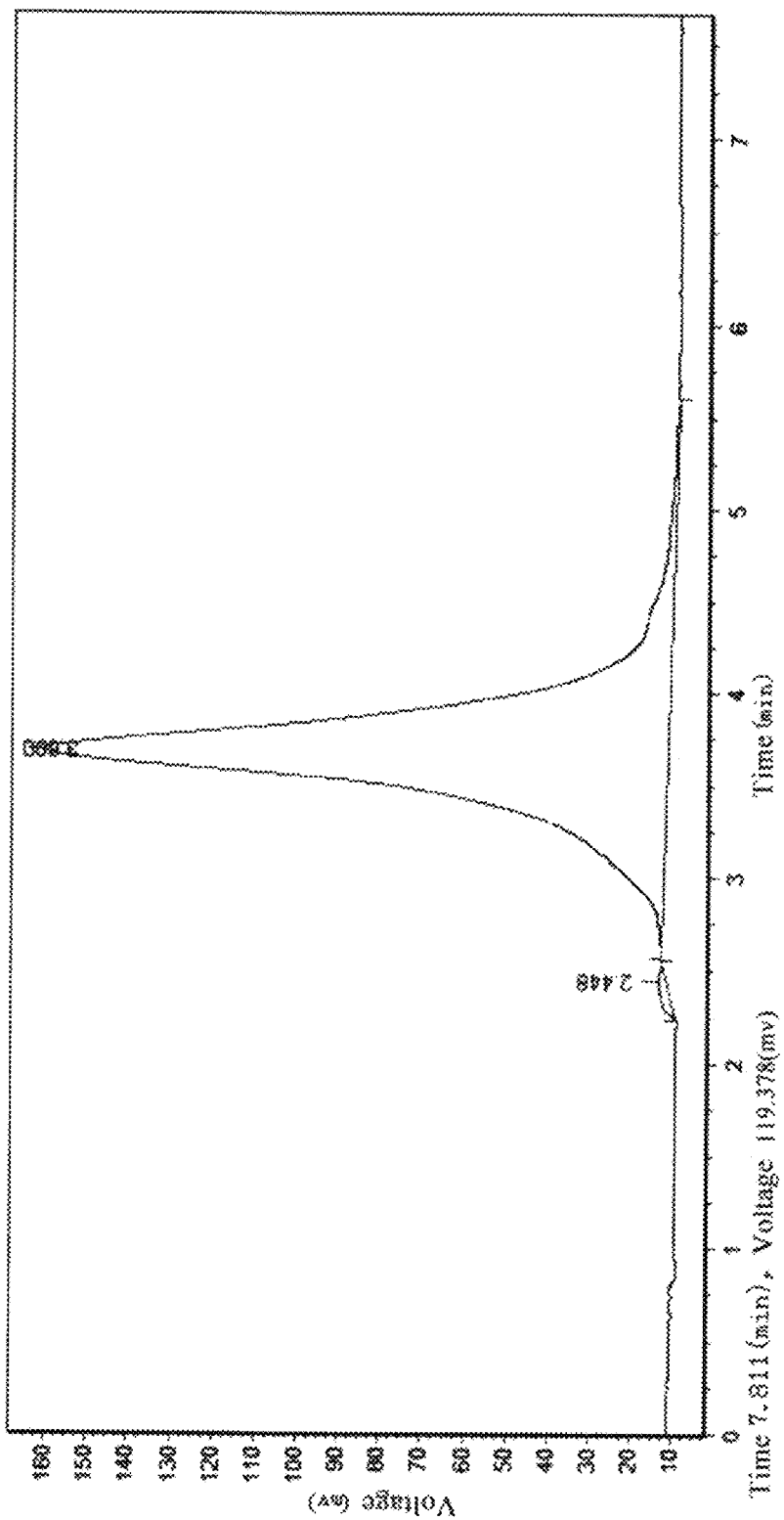

Ultraviolet-visible detection is applied in the present invention:
Analysis wavelength: 245 NM
Detection sample: tea: Taheebo produced in Japan
Detection environment: chromatographic column: C18; mobile phase: 100% methyl alcohol; flow velocity: 0.6 ml/min
Chromatogram obtained after the detection is as shown in FIG. 17.

In brief: chromatograms of several kinds of tea are tested, and only one main peak is highly contained. The difference exists because components of low content are not quite the same.

Embodiment 13

Figure 18:
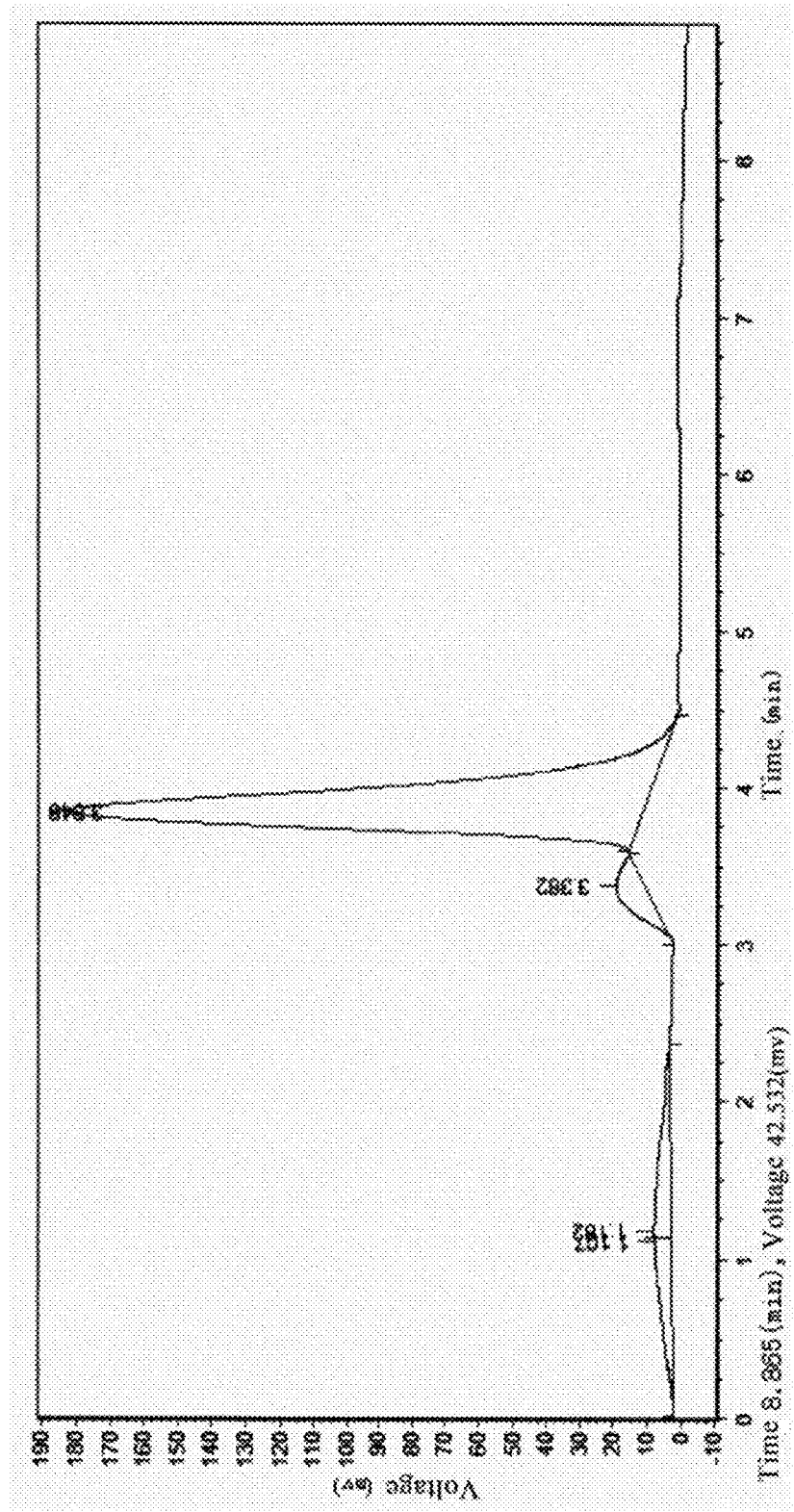

Ultraviolet-visible detection is applied in the present invention:
Analysis wavelength: 254 NM
Detection sample: pure sesame oil
Detection environment: chromatographic column: C18; mobile phase: 100% methyl alcohol; flow velocity: 0.6 ml/min
Chromatogram obtained after the detection is as shown in FIG. 18.

In brief: the chromatogram shows that apart from a main peak of high content, there are some components of low content. Further, detection of possibility of other edible oil or illegal cooking oil can be tested.

Embodiment 14

Figure 19:
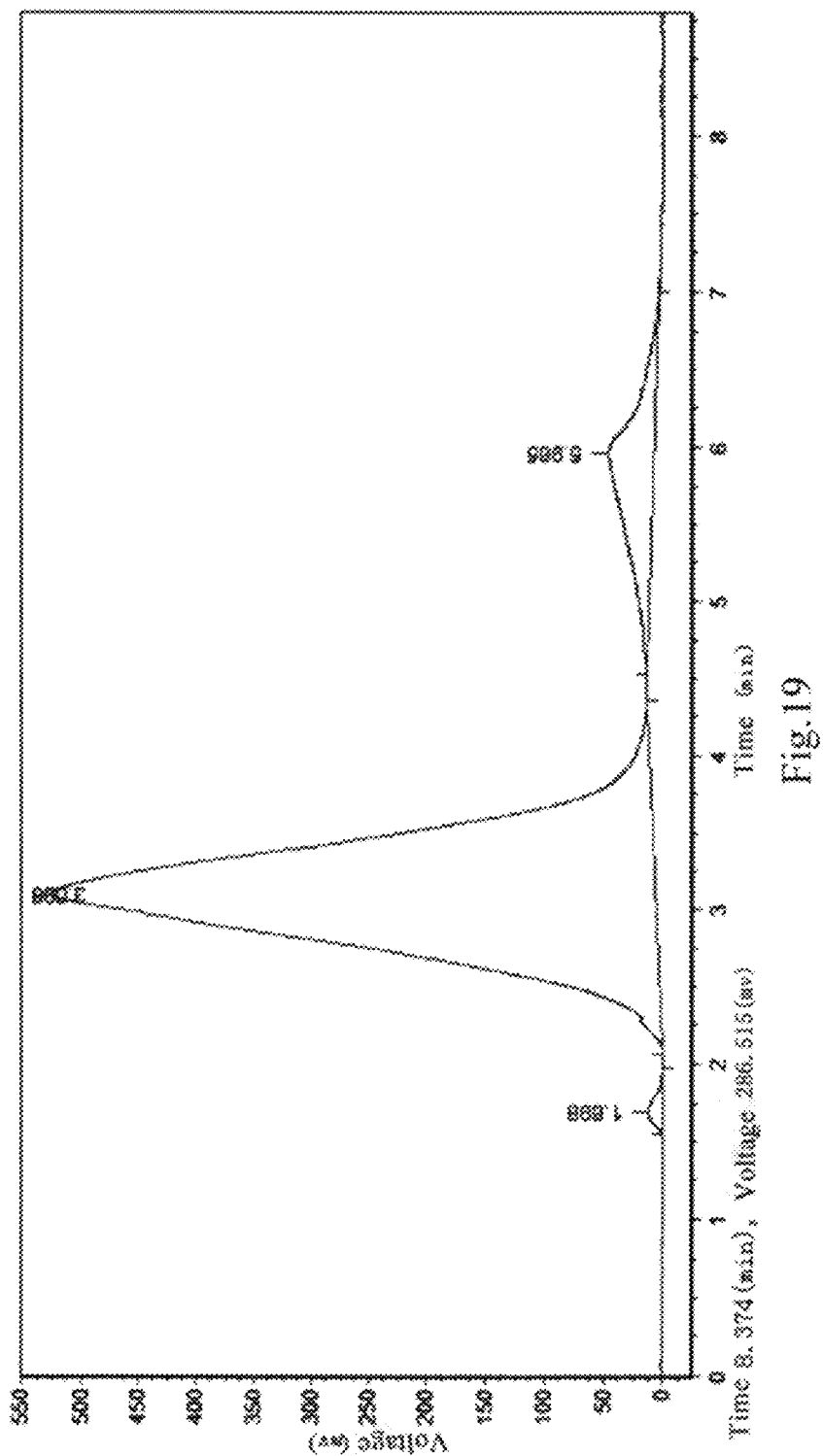

Ultraviolet-visible detection is applied in the present invention:
Analysis wavelength: 248 NM
Detection sample: high-grade wine: Moutai made in China
Detection environment: chromatographic column: C18; mobile phase: 100% methyl alcohol; flow velocity: 1 ml/min
Chromatogram obtained after the detection is as shown in FIG. 19.

In brief: Moutai is a famous wine in China. High content of alcohol means the high purity. Moreover, whether there are other components of low content can be seen by using exclusion and comparison experiment methods to protect the quality.

According to the chromatogram of the said 1~14 embodiments, the ultraviolet-visible and fluorescence double monochromatic light dual detector involved in the present invention can be used for the detection of the ultraviolet-visible wavelengths and fluorescence double monochromatic light. Besides, it has extremely excellent sensitivity and stability for detection. Especially embodiment 1 (wavelength: 210 NM and 254 NM have obvious absorption for naphthalene sample which generates photoelectric signals), it proves that it goes against "Beer Lambert Law" for the said "DAD diode array ultraviolet detector" in the background of the invention to eliminate spectroscopical mechanism of monochromatic device in the front of sample detection cell and at the same time, incidence of hybrid light of various wavelengths into sample detection cell will generate other false high sensitivity superposed signals of various wavelengths; Meanwhile, it proves that the present invention cannot find similar products with such excellent sensitivity and stability (extremely small noise and drift) in the most difficult far ultraviolet edge wavelength 210 NM range. Furthermore, excellent sensitivity and stability in the whole wavelength range has been proved, and various disadvantages in existing technical ultraviolet detection products have been overcome; in addition, situations related to fluorescence detection in embodiments 4~6 have proven that the present invention has overcome technical problems (noise and drift signals are far larger than ultraviolet detection by 4~5 orders of magnitudes) of high-grade double monochromatic mechanism in fluorescence detection. Moreover, apart from adopting the xenon lamp, the present art takes the first to use deuterium lamp as the light source of fluorescence detection, creating an innovative high performance double monochromatic fluorescence detector, so that sensitivity and stability in the present invention possesses much more excellent performance than that of standards.

It should be understood that for common technical personnel in this field, changes or improvements can be made according to the said description, while such changes and improvements should belong to the scope of protection of claims attached in the present invention.

What is claimed is:

1. A both ultraviolet-visible and double monochromatic fluorescence dual detector for HPLC, comprising:
a casing having a power supply socket, a sample solution inlet and an outlet, a control panel with operation keyboard and liquid crystal display, and a detection signal output interface being set on the casing, a detection optical member and a detection electromechanical member being set inside the casing;
said detection optical members including a first monochromatic spectroscopic device—raster (G1) used for both ultraviolet-visible wavelength and fluorescence excitation wavelength, a second monochromatic spectroscopic device—raster (G2) used for secondary fluorescence emission wavelength, a light source, four groups of lens needed for processing the light paths, two groups of photosensitive diode for receiving ultraviolet and fluorescence photoelectric signals respectively, and an individual sample detection cell shared by ultraviolet and fluorescence detections which is connected with said sample solution inlet and outlet;

said detection electromechanical member comprising:

a central controller: which is consisted of microcomputers and program executor, and is connected with the operation keyboard and the liquid crystal display of the control panel, the central controller executes and controls according to the selected operational key, and display selected optical wavelength, voltage, and value of sensitivity on the liquid crystal display;

a preposed amplifying module including a first operational amplifier whose inverting input terminal is connected with the parallel connection junctions of the negative terminal of photosensitive diode and non-inverting input terminal is connected with the earth, positive terminals of two photosensitive diodes are controlled by the central controller through a first shift switch (K1) of a first relay and are earthed, a first output terminal is connected with a fixed head of a second shift switch (K2) of the first relay, the first and the second shift switches which are mutually synchronized, two resistances maintaining feedback are corresponding to working state of the ultraviolet and fluorescence detection respectively, converting input photocurrent signals into voltage signals in the preposed amplifying module and then amplifying them;

an auto gain modules including an analog/digital-digital/analog convertor (1) and a digital/analog convertor (2), as the central controller operates in a digital method, analog voltage signals of the first output terminal of the proposed amplifying module are input into the auto gain module to be amplified and subtracted digitally by the analog/digital-digital/analog convertor (1) controlled by the said central controller, thereby, for ultraviolet detection voltages of the output terminal of the analog/digital-digital/analog convertor (1) for every wavelength being controlled in a constant value in the whole wavelength range is realized; the central controller deposits digital signals of the analog/digital-digital/analog convertor (1) in the digital/analog convertor (2), and the digital/analog convertor (2) conducts a subtraction to digital signals in dynamic state and digital signals in static state;

a noise processing module including a second operational amplifier, whose in-phase input terminal is connected with the output terminal of the analog/digital-digital/analog convertor (1), after the central controller makes subtraction to the two digital signals in dynamic and static state in the digital/analog convertor (2), a converted different voltage of the output terminal of the digital/analog convertor (2) will be transmitted randomly to the inverting input terminal of the second operational amplifier to be used for the elimination of the noise and drift of the instrument;

a logarithm amplifying nodule, an input terminal of the logarithm amplifying module is connected with a second output terminal of the second operational amplifier, and a position of a third shift switch of the second relay is driven by the central controller, and during an ultraviolet detection period a third operational amplifier and double transistors (Tr1 and Tr2) will conduct logarithm processing, and a fourth operational amplifier conducts amplifying and output operation; during a fluorescence detection period, voltage signals of the second output terminal of the second operational amplifier of the noise processing module are directly amplified through the fourth operational amplifier and then the amplified sample voltage signal is output through the detection signal output interface.

2. The both ultraviolet-visible and double monochromatic fluorescence dual detector for HPLC according to claim 1, characterized in that: the preposed amplifying module further includes a first resistance and a second resistance, a first terminal of the first and second resistance is respectively connected with the first inverting input terminal a second terminal of the first and second resistance is connected with the first output terminal through the first and second shift switches of the first relay, while an ultraviolet U and fluorescence F operational keys on the panel is pressed according to the need of the analysis on the ultraviolet and fluorescence, the central controller drives the first relay.

3. The both ultraviolet-visible and double monochromatic fluorescence dual detector for HPLC according to claim 1, characterized in that the first operational amplifier is an operational amplifier with high input impedance and low drift.

4. The both ultraviolet-visible and double monochromatic fluorescence dual detector for HPLC according to claim 1, characterized in that the said noise processing module further includes a third resistance, a fourth resistance, a fifth resistance, and a first capacitor, a second inverting input terminal of the second operational amplifier is connected with the output terminal of the digital analog convertor (2) through the fourth resistance, and the second in-phase input terminal of the second operational amplifier is connected with the output terminal of the analog/digital-digital/analog convertor 1 through the third resistance, and the second output terminal of the second operational amplifier is connected with the input terminal of the logarithm amplifying module, and one terminal of the fifth resistance is connected with the second inverting input terminal and the other terminal is connected with the second output terminal, and the said first capacitor is connected in parallel with the fifth resistance.

5. The both ultraviolet-visible and double monochromatic fluorescence dual detector for HPLC according to claim 1, characterized in that the said logarithm amplifying module further includes a sixth resistance, a seventh resistance, an eighth resistance, a ninth resistance, and a tenth resistance, an inverting input terminal of the third operational amplifier is connected with the second output terminal through the sixth resistance and also connected with the collector electrode of the transistor (Tr1), the third in-phase input terminal and the base electrode of the transistor (Tr1) are earthed, and one terminal of the seventh resistance is connected with the third output terminal while the other terminal connected with the two emitter electrodes of the double transistor, and the two terminals of the eighth resistance are respectively connected with the collector electrode and the base electrode of the transistor (Tr2) and DC voltage +V and an inverting input terminal of the fourth operational amplifier is connected with one terminal of a ninth and one terminal of a tenth resistance respectively, and the other terminal of the ninth resistance is connected with the fourth output terminal while the other terminal of the tenth resistance is earthed, and the in-phase input terminal of the fourth operational amplifies is connected with the fixed head of the third shift switch of the second relay.

6. The both ultraviolet-visible and double monochromatic fluorescence dual detector for HPLC according to claim 1, characterized in that the light source of the dual detector mentioned comprises a stable and low energy-consumption deuterium lamp.

7. The both ultraviolet-visible and double monochromatic fluorescence dual detector for HPLC according to claim 1, characterized in that: the said sample detection cell has functions of both direct-irradiation and radiation with light transmission, and is composed of quartz cells with leak-proofness for mobile phase and sample solution, suitable for both ultraviolet-visible and double monochromatic fluorescence dual detector for HPLC with sample distinguishing ability and 10 microliters of extremely small sample detection cell volume.

8. The both ultraviolet-visible and double monochromatic fluorescence dual detector for HPLC according to claim 2, characterized in that: the said first operational amplifier is an operational amplifier with input impedance and low drift.

* * * * *